United States Patent
Wright et al.

(10) Patent No.: US 6,566,514 B1
(45) Date of Patent: May 20, 2003

(54) OLIGONUCLEOTIDE SEQUENCES COMPLEMENTARY TO THIOREDOXIN OR THIOREDOXIN REDUCTASE GENES AND METHODS OF USING SAME TO MODULATE CELL GROWTH

(75) Inventors: Jim A. Wright, Aurora (CA); Aiping H. Young, North York (CA); Yoon S. Lee, Mississauga (CA)

(73) Assignee: GeneSense Technologies Inc., Toronto (CA)

( * ) Notice: Subject to any disclaimer, the term of this patent is extended or adjusted under 35 U.S.C. 154(b) by 0 days.

(21) Appl. No.: 09/601,144

(22) PCT Filed: Jan. 29, 1999

(86) PCT No.: PCT/CA99/00077

§ 371 (c)(1),
(2), (4) Date: Oct. 18, 2000

(87) PCT Pub. No.: WO99/38963

PCT Pub. Date: Aug. 5, 1999

Related U.S. Application Data

(60) Provisional application No. 60/073,196, filed on Jan. 30, 1998.

(51) Int. Cl.[7] .................... C07H 21/04; C07H 21/02; C12Q 1/68; C12P 19/34; C12N 15/85
(52) U.S. Cl. .................. 536/24.5; 536/24.3; 536/24.31; 536/24.33; 435/6; 435/91.1; 435/325; 435/375
(58) Field of Search .................... 435/6, 91.1, 91.3, 435/325, 375; 536/23.1, 23.2, 24.5, 24.3, 24.33, 24.31; 514/44

(56) References Cited

U.S. PATENT DOCUMENTS

| | | | |
|---|---|---|---|
| 4,666,828 A | 5/1987 | Gusella | |
| 4,683,202 A | 7/1987 | Mullis | |
| 4,801,531 A | 1/1989 | Frossard | |
| 5,011,472 A | 4/1991 | Aebischer et al. | |
| 5,023,252 A | 6/1991 | Hseih | |
| 5,034,506 A | 7/1991 | Summerton et al. | |
| 5,192,659 A | 3/1993 | Simons | |
| 5,225,347 A | 7/1993 | Goldberg et al. | |
| 5,272,057 A | 12/1993 | Smulson | |
| 5,580,859 A | 12/1996 | Felgner et al. | |
| 5,719,262 A | 2/1998 | Buchardt et al. | |
| 5,766,855 A | 6/1998 | Buchardt et al. | |
| 5,801,154 A | * 9/1998 | Baracchini et al. | 514/44 |
| 5,831,049 A | * 11/1998 | Hillman et al. | 536/23.1 |

FOREIGN PATENT DOCUMENTS

| | | |
|---|---|---|
| WO | WO91/04320 | 4/1991 |
| WO | WO98/24472 | 6/1998 |

OTHER PUBLICATIONS

Branch, A., "A good antisense molecule is hard to find", TIBS 23, Feb. 1998, pp. 45–50.*

Agrawal, S. "Antisense Oligonucleotides: Towards Clinical Trials", *TIBTECH,* vol. 14, Oct. 1996, pp. 376–387.*

Crooke, S, "Antisense '97: A roundtable on the state of the industry", Nature Biotechnology, vol. 15 Jun. 1997, pp. 519–528.*

Abate, C., et al., (1990) "Redox regulation of Fos and Jun DNA–binding activity in vitro", *Science* 249:1157–1161.

Agarwal, et al., (1995) "Reconstitution of signal transduction from the membrane to the nucleus in a baculovirus expression system: activation of Raf–1 leads to hypermodification of c–jun and c–fos via multiple pathways", *Oncogene* 11:427–438.

Agawal, (1996) "Antisense oligonucleotides: towards clinical trials", *TIBTECH* 14:376–387.

Akhtar, S., et al., (1991) "Interactions of antisense DNA olidonucleotide analogs with phospholipid membranes (liposomes)", *Nuc.Acids Res.* 19(20):5551–5559.

Alma, A., et al., (1997) "Antisense oligonucleotides as therapeutic agents", *Pharmacol. Res.* 36(3):171–178.

Alemi, J., et al., (1996), "A novel deletion in the RET proto–oncogene found in sporadic medullary thyroid carcinoma", *Anticancer Research* 16:2619–2622.

Altschul, et al., (1990) "Basic local alignment search tool", *J. Mol. Biol.* 215:403–410.

Anazodo, M.I., et al., (1995) "Antiviral activity and protection of cells against human immunodeficiency virus type–1 using an antisense oligodeozyribonucleotide phosphorothioate complementary to the 5'–LTR region of the viral genome", *Gene* 166:227–232.

Anazodo, M.I., et al., (1995) "Sequence–specific inhibition of gene expression by a novel antisense oligodeozynucleotide phosphorothioate directed against a nonregulatory region of the human immunodeficiency virus type 1 genome" J. Virol. 69(3):1794–1801.

Anazodo, M.I., et al., (1995), "Inhibition of human immunodeficiency virus type 1 (HIV) gag gene expression by an antisense oligodeoxynucleoride phosphorothioate" *Leukemia* 9(1):S86–S88.

Anazodo, M.I., et al., (1996) "Relative levels of inhibition of p24 gene expression by different 20–mer antisense oligonucleotide sequences targeting nucleotides + 1129 to + 1268 of the HIV–gag genome: An analysis of mechanism", *Biochem. Biophys. Res. Commun.* 229:305–309.

(List continued on next page.)

*Primary Examiner*—Sean McGarry
*Assistant Examiner*—Karen A Lacourciere
(74) *Attorney, Agent, or Firm*—Gary M. Nath; Todd L. Juneau; Joshua B. Goldberg

(57) ABSTRACT

This invention relates to oligonucleotides complementary to the thioredoxin and thioredoxin reductase genes which modulate tumor cell growth in mammals. This invention is also related to methods of using such compounds in inhibiting the growth of tumor cells in mammals. This invention also relates to pharmaceutical compositions comprising a pharmaceutically acceptable excipient and an effective amount of a compound of this invention.

13 Claims, 23 Drawing Sheets

OTHER PUBLICATIONS

Anazodo, M.I., et al., (1997) "Characterization of GP12A, a potent inhibitor of HIV–1 gene expression and viral replication", *Nucleosides and Nucleotides* 16(7–9):1241–1249.

Baker, et al., (1997) "Thioredoxin, a gene found overexpressed in human cancer, inhibits apoptosis in vitro and in vivo", *Cancer Res.* 57:5162–5167.

Bannister, A.J., et al., (1991) "In vitro DNA binding activity of Fos/Jun and BZLF1 but not CEBP is affected by redox changes", Oncogene 6:1243–1250.

Berggren, et al., (1996) "Thioredoxin and thioredoxin reductase gene expression in human tumors and cell lines, and the effects of serum stimulation and hypoxia", *Anticancer Res.* 16:3459–3466.

Blaese, (1997) "Gene therapy for cancer", *Scientific American* 276(6):111–115.

Blasco, M.A., et al., (1997) "Telomere shortening and tumor formation by mouse cells lacking telomerase RNA", *Cell* 91:25–34.

Boven, et al, (1992) "Phase II preclinical drug screening in human tumor xenografts: A first European multicenter collaborative study" *Cancer Res.* 52:5940–5947.

Bui, T.D. et al, (1997) *Oncogene* 14(10):1249–1253.

Calabretta, et al., (1996) "Antisense strategies in the treatment of leukemias", *Semin. Oncol* 23(1):78–87.

Carlomagno, C., et al., (1996) "c–erbB2 overexpression decreases the benefit of adjuvant tamoxifen in early–stage breast cancer without axillary lymph node metastases" *J. Clin Oncol* 14(10):2702–2708.

Chang, C.P., et al., (1997) "The hox cooperativity motif of the chimeric oncoprotein E2a–Pbx1 is necessary and sufficient for oncogenesis", *Mol. Cell. Biology* 17(1):81–88.

Choy, et al., (1988) "Molecular mechanisms of drug resistance involving ribonucleotide reductase: hydroxyurea resistance in a series of clonally related mouse cell lines selected in the presence of increasing drug concentrations", *Cancer Res.* 48:2029–2035.

Chu, C.T., et al., (1997) "Receptor dimerization is not a factor in the signalling activity of a transforming variant epidermal growth factor receptor (EGFRvIII)", *Biochem. J.* 324:855–861.

Cole, et al., (1992) "Overexpression of a transporter gene in a multidrug–resistant human lung cancer cell line", *Science* 258:1650–1654.

Counter, C.M., et al., (1994) "Telomerase activity in human ovarian carcinoma" *Proc. Natl. Acad. Sci USA* 91:2900–2904

Cromlish, J.A., et al., (1989) "Human Transcription Factor IIIC (TFIIIC): purification, polypeptide structure, and the involvement of thiol groups in specific DNA binding", *J. Biol. Chem.* 264(30):18100–18109.

Crooke, (1995) "Progress in antisense therapeutics", *Hematol Pathol.* 9(2):59–72.

Crooke, S.T., et al., (1996) "Progress in antisense oligonucleotide therapeutics", *Annu. Rev. Pharmacol. Toxicol.* 36:107–129.

Curcio, et al., (1997) "Oligonucleotides as modulators of cancer gene expression", *Pharmacol Ther.* 74(3):317–332.

Dedera, D.A., et al., (1993) "Chimeric homeobox gene E2A–PBX1 induces proliferation, apoptosis, and malignant lymphomas in transgenic mice", *Cell* 74:833–843.

Deiss, L.P. and Kimchi, A., (1991) "A genetic tool used to identify thioredoxin as a mediator of a growth inhibitory signal", *Science* 252:117–120.

Devereux, J., et al., (1984) "A comprehensive set of sequence analysis programs for the VAX", *Nucleic Acids Res.* 12(1):387–395.

Eckstein, (1985) "Nucleoside phosphorothiotes", *Ann Rev. Biochem.* 54:367–402.

Engman, et al., (1997) "Diaryl chalcogenides as selective inhibitors of thioredoxin reductase and potential antitumor agents", *Anticancer Res.* 17:4599–4605.

Fan, et al., (1996) "Ribonucleotide reductase R2 component is a novel malignancy determinant that cooperates with activated oncogenes to determine transformation and malignant potential", *Proc. Natl. Acad. Sci USA* 93:14036–14040.

Felgner, (1997) "Nonviral strategies for gene therapy", *Scientific American,* Jun. 1997, pp. 102–106.

Fujii, S., et al., (1991) "Coexpression of adult T–cell leukemia–derived factor, a human thioredoxin homologue, and human papillomavirus DNA in neoplastic cervical squamous epithelium", *Cancer* 68(7):1583–1591.

Galaktionov, K., et al., (1995) "CDC25 phosphatases as potential human oncogenes", Science 269:1575–1577.

Gallegos et al., (1997) "Mechanisms of the regulation of thioredoxin reductase activity in cancer cells by the chemopreventive agent selenium", *Cancer Res.* 57:4965–4970.

Gallegos, et al., (1996) "Transfection with human thioredoxin increases cell proliferation and a dominant–negative mutant thioredoxin reverses the transformed phenotype of human breast cancer cells", *Cancer Res.* 56:5765–5770.

Gasdaska, J.R., et al., (1995) "Cell growth stimulation by the redox protein thioredoxin occurs by a novel helper mechanism", *Cell Growth Differ.* 6:1643–1650.

Gasdaska, P.Y., et al., (1994) "The predicted amino acid sequence of human thioredoxin is identical to that of the autocrine growth factor human adult T–cell derived facto (ADF): thioredoxin mRNA is elevated in some human tumors", *Biochim. Biophys. Acta* 1218:292–296.

Gasdaska, P.Y., et al., (1995) "Cloning and sequencing of a human thioredoxin gene", *FEBS Lett.* 373:5–9.

Gasparotto, D., et al., (1997) "Overexpression of CDC25B in head and neck cancers", *Cancer Research* 57:2366–2368.

Gerwirtz, (1993) "Olidogeoxynucleotide–based therapeutics for human leukemias", *Stem Cells* 11(suppl 3): 96–103.

Giovanella, et al., (1983) "Correlation between response to chemotherapy of human tumor in patients and in nude mice", *Cancer* 52:1146–1152.

Gladyshev, V.N., et al., (1998) "Constrasting patterns of regulation of the antioxidant selenoproteins, thioredoxin reductase, and glutathione peroxidase, in cancer cells" *Biochem. Biophys. Res. Commun.* 251:488–493.

Good and Nielsen, (1998) "Inhibition of translation and bacterial growth by peptide nucleic acid targeted to ribosomal RNA", *Proc. Natl. Acad. Sci USA* 95:2073–2076.

Grippo, J.F., et al., (1983) "Proof that the endogenous heat–stable gluocorticoid receptor–activating factor is thioredoxin", *J. Biol. Chem.* 260(1):93–97.

Grippo, J.F., et al., (1983) "Evidence that the endogenous heat–stable gluocorticoid receptor–activating factor is thioredoxin", *J. Biol. Chem.* 258(22):13658–13664.

Hampel, et al., (1989) "RNA catalytic properties of the minimum (–)s TRSV sequence", *Biochemistry* 28:4929–4933.

Hanania, et al., (1995) "Recent advances in the application of gene therapy to human disease", *Am. J. Med* 99:537–552.

Hardiman, G., et al., (1997) "Isolation, characterization and chromosomal localization of human WNT10B", *Cytogenet. Cell Genet.* 77:278–282.

Hariharan, J. et al., (1996) "Alternative forms of the human thioredoxin mRNA: identification and characterization", *Gene* 173:265–270.

Hayashi, S. et al., (1997) "Functional modulation of estrogen receptor by redox state with reference to thioredoxin as a mediator", *Nucleic Acids Res.* 25(20):4035–4040.

Ho, P.T., et al., (1997) "Antisense oligonucleotides as therapeutics for malignant diseases", *Semin. Oncol.* 24(2):187–202.

Holmgren, A., (1984) "Enzymatic reduction–oxidation of protein disulfides by thioredoxin", *Methods Enzymol.* 107:295–300.

Holmgren, A., (1985) "Thioredoxin", *Ann. Rev. Biochem.* 54:237–271.

Holmgren, A., (1989) "Thioredoxiin and glutaredoxin systems", *J. Biol. Chem.* 264(24):13963–13966.

Huang and Wright, (1994) "Fibroblast growth factor mediated alterations in drug resistance, and evidence of gene amplification", *Oncogene* 9:491–499.

Hurta and Wright, (1995) "Malignant transformation by H–ras results in aberrant regulation of ribonucleotide reductase gene expression by transforming growth factor–beta," *J. Cell, Biochem.* 57:543–556.

Iyer, et al., (1990) "The automated synthesis of sulfur–containing oligodeoxyribonucleotides using 3H–1, 2–benzodithiol–3–one 1,1–dioxide as a sulfur–transfer reagent", *J. Or. Chem.* 55(15):4693–4699.

James, W., (1991) "Towards gene–inhibition therapy: A review of progress and prospects in the filed of antiviral antisense nucleic acids and ribozymes", *Antiviral Chemistry & Chemother.* 2(4):191–214.

Katsumata, M., et al., (1995) "Prevention of breast tumour development in vivo by downregulation of the p185$^{neu}$ receptor", *Nature Med.* 1(7):644–648.

Kawahara, et al., (1996) "Enhanced coexpression of thioredoxin and high mobility group protein 1 genes in human hepatocellular carcinoma and the possible association with decreased sensitivity to cisplatin", *Cancer Res.* 56:5330–5333.

Khosravi–Far, R., et al., (1998) "Increasing complexity of Ras signal transducation: Involvement of Rho family proteins", *Adv. Cancer Research* 72:57–107.

Kunkel, M.W. et al., (1997) "Cell line–directed screening assay for inhibitors of thioredoxin reductase signaling as potential anti–cancer drugs." *Anti–Cancer Drug Design* 12:659–670.

Lee, S.S., et al. (1998) "Binding of human virus oncoproteins to hDlg/SAP97, a mammalian homolog of the Drosophila discs larger tumor suppressor protein", *Proc. Natl. Acad. Sci, USA* 94:6670–6675.

Lefebvre–d'Hellencourt, et al., (1995) "Immunomodulation by cytokine antisens oligonucletides", *Eur. Cytokine Netw.* 6(1):7–19.

Lev–Lehman, et al., (1997) "Antisense oligomers in vitro and in vivo", in: *Antisense Therapeutics,* A. Cohen and S. Smicek (eds.), Plenum Press, New York, NY.

Loke, et al., (1989) "Characterization of oligonucleotide transport into living cells", *Proc. Natl. Acad. Sci. USA* 86:3473–3478.

Lundstrom, J., et al., (199) "Protein disulfide–isomerase is a substrate for thioredoxin reductase and has thioredoxin–like activity", *J. Biol. Chem.* 265(16):9114–9120.

Magi–Galluzzi, C., et al., (1997) "Mitogen–activated protein kinase phosphatase 1 is overexpressed in prostate cancers and is inversely related to apoptosis", *Lab. Invest.* 76(1):37–51.

Makino, Y., et al. (1996)"Thioredoxin: A redox–regulating cellular cofactor for glucorticoid hormone action", *J. Clin. Invest.* 98(11):2469–2477.

Marengo, S.R. et al., (1997) "Metastasis induced by overexpression of p185$^{neu-T}$ after orthotopic injection into a prostatic epithelial cell line (Nbe)" *Mol. Carcinog.* 19:163–175.

Marwick, C., (1998) "First 'antisense' drug will treat CMV Retinitis", *JAMA.* 280(10):871.

Matthews, J.R., et al., (1992) "Thioredoxin regulates the DNA binding activity of NF–B by reduction of a disulphide bond involving cysteine 62", *Nucleic Acids Res.* 20(15):3821–3830.

Mau and Powis, (1992) Inhibition of cellular thioredoxin reductase by diaziquone and doxorubicin. Relationship to the inhibition of cell proliferation and decreased ribonucleotide reductase activity:, *Biochem. Pharmacol.* 43(7):1621–1626.

Mau and Powis, (1992) "Mechanism–based inhibition of thioredoxin reductase by antitumor quinoid compounds", *Biochem. Pharmacol.* 43(7):1613–1620.

McClarty, G.A. 35 al., (1990) "Increaseed ferritin gene expression is associated with increased ribonucleotide reductase gene expression and the establishment of hydroxyurea resistance in mammalian cells" *J. Biol. Chem.* 265(13):7539–7547.

Meyerson, M., et al., (1997) "hEST2, the putative human telomerase catalytic subunit gene, is up–regulated in tumor cells and during immortalization", *Cell* 90:785–795.

Mitsuhashi, M., (1997) "Strategy for designing specific antesense oligonucleotide sequences", *J. Gastroenterol.* 32:282–287.

Morrison, (1991) "Suppression of basic fibroblast growth factor expression by antisense oligodeoxynucleotides inhibits the growth of transformed human astorcytes", *J. Biol. Chem.* 266(2):728–734.

Nakamura, H., et al., (1992) "Expression and growth–promoting effect of adult t–cell leukemia–derived factor", *Cancer* 69:2091–2097.

Nakamura, H., et al., (1994) "Adult T cell leukemia–derived factor/human thioredoxin protects endothelial F–2 cell injury caused by activated neutrophils or hydrogen peroxide" [published erratum appears in *Immunol. Lett.*, 1994 Oct.; 42(3):213], *Immunol. Lett.* 42:75–80.

Narayanan and Akhtar, (1996) "Antisense therapy", *Curr. Opin. Oncol.* 8:509–515.

Newman, G.W. et al., (1994) "Opposing regulatory effects of thioredoxin and eosinophil cytotoxicty–enhancing factor on the development of Human Immunodeficiency Virus 1", *J. Exp. Med.* 180:359–363.

Nielsen, et al., (1991) "Sequence–selective recognition of DNA by strand displacement with a thymine–substituted polyamide", *Science* 254:1497–1500.

Oblong, J.E., et al., (1994) "Site–directed mutagenesis of active site cysteines in human thioredoxin produces competitive inhibitor of human thioredoxin reductase and elimination of mitogenic properties of thioredoxin", *J. Biol. Chem.* 269(16):11714–11720.

Okuno, H., et al., (1993) "Escape from redox regulation enhances the transforming activity of Fos", *Oncogene* 8:695–701.

Powis, G. et al., (1994) "The thioredoxin/thioredoxin reductase redox system and control of cell growth" *Oncol. Res.* 6:539–544.

Radhakrishnan, et al., (1990) "The automated synthesis of sulfur–containing oligodeoxyribonucleotides using 3H–1, 2–benzodithiol–3–one 1,1 dioxide as a sulfur–transfer reagent", *J. Org. Chem.* 55:4693–4699.

Rosolen, et al., (1990) "Antisense inhibition of single copy N–myc expression results in decreased cell growth without reduction of c–myc protein in a neuroepitheliom cell line", *Cancer Res.* 50:6316–6322.

Rummel, M.M., et al., (1996) "Phorbol ester and cyclic AMP–mediated regulation of the melanoma–associated cell adhesion molecule MUC18/MCAM", *Cancer Research* 56(9):2218–2223.

Saitoh, M. et al. (1998) "Mammalian thioredoxin is a direct inhibitor of apoptosis signal–regulating kinase (ASK) 1" *EMBO J.* 17(9):2596–2606.

Sarver, et al. (1990) *Gene Regulation and AIDS,* pp. 305–325.

Scanlon, et al., (1995) "Oligonucleotide–mediated modulation of mammalian gene expression", *FASEB J.* 9:1288–1296.

Schabet and Herrlinger (1998) "Animal models of leptomeningeal metastasis" *J. Neuro–Oncology* 38:199–205.

Schallreuter, K.U., et al., (1986) "The role of thioredoxin reductase in the reduction of free radicals at the surface of the epidermis", *Biochem. Biophys. Res. Commun.* 136(2):630–637.

Schallreuter, K.U., et al., (1989) "The stereospecific suicide inhibition of human melanoma thioredoxin reductase by 13–cis retinoic acid", *Biochem Biophys. Res. Commun.* 160(2):572–579.

Schallreuter, K.U., et al., (1991) "New aspects in the pathophysiology of cutaneous melanoma: a review of the role of thioproteins and the effect of nitrosoureas", *Melanoma Res.* 1:159–167.

Shaw, J.W., et al., (1991) "Modified deoxyoligonucleotides stable to exonuclease degradation in serum", *Nucleic Acids Res.* 19(4):747–750.

Shay, J.W., et al., (1997) "A survey of telomerase activity in human cancer", *European J. Cancer* 33(5):787–791.

Shintani, S., et al., (1995) "Expression of C–erbB family gene products in adenoid cystic carcinoma of salivary glands: An immunohistochemical study", *Anticancer Research* 15:2623–2626.

Skorski, T., et al., (1995) "Phosphatidylinositol–3 kinase activity is regulated by BCR/ABL and is required for the growth of philadelphia chromosome–positive cells", *Blood* 86(2):726–736.

Spector, A., et al., (1988) "The effect of $H_2O_2$ upon thioredoxin–enriched lens epithelial cells", *J. Biol. Chem.* 263(10):4984–4990.

Spitzer, et al., (1988) "Inhibition of deoxyribonucleases by phosphorothioate groups in oligodeoxyribonucleotides", *Nucleic Acids Res.* 18(24):11691–11704.

Spyrou, G., et al., (1997) "Cloning and expression of a novel mammalian thioredoxin", *J. Biol. Chem.* 272(5):2936–2941.

Szekeres, T., et al, (1997) "The enzyme ribonucleotide reductase: Target for antitumor and anti–HIV therapy", *Crit. Rev.Clin. Lab. Sci.* 34(6):503–528.

Tagaya, et al., (1989) "ATL–derived factor (ADF), an IL–2 receptor/Tac inducer homologous to thioredoxin; possible involvement of dithiol–reduction in the IL–2 receptor induction", *EMBO J.* 8(3):757–764.

Tagaya, et al., (1994) "ATL–derived factor (ADF) and IL–2–receptor/Tac inducer homologous to thioredoxin; possible involvement of dithiol–reduction in the IL–2 receptor induction", *EMBO J.* 13(9):2244.

Testoni, et al., (1996) "A New method of "in–cell reverse transciptse–polymerase chain reaction" for the detecion of BCR/ABL transcript in chronic myeloid leukemia patients", *Blood* 87(9):3822–3827.

Thelander, L., et al., (1979) "Reduction of ribonucleotides", *Annu. Rev. Biochem.* 48:13–158.

Uhlenbeck, (1987) "A small catalytic oligoribonucleotide", *Nature* 328:596–600.

U–Taniguchi et al, (1995) "Cell cycle inhibition of HTLV–I transformed T cell lines by retinoic acid: the possible therapeutic use of thioredoxin reductase inhibitors", *Oncol. Res.* 7(3/4):183–189.

Wagner, (1994) "Gene inhibition using antisense oligodeoxynucleotides", *Nature,* 372:333–335.

Wagner, R. W., (1995) "The state of the art in antisense research", *Nat. Med.* 1(11):1116–1118.

Wagner, R.W.,, et al., (1996) "Potent and selective inhibition of gene expression by an antisense heptanucleotide", *Nature Biotechnology* 14:840–844.

Wang, J., et al., (1997) "Possible roles of an adult T–cell leukemia (ATL) derived factor/thioredoxin in the drug resistance of ATL to adriamycin", *Blood* 89(7):2480–2487.

Weber, G., (1983) "Biochemical strategy of cancer cell and the design of chemotherapy: G.H.A. Clowes Memorial Lecture", *Cancer Research* 43:3466–3492.

Weber, G., et al., (1996) "Current issues in the regulation of signal transduction", *Adv. Enzyme Regulation* 36:33–55.

Weber, G., et al., (1996) "Increased signal transduction activity and down–regulation in human cancer cells", *Anticancer Research* 16:3271–3281.

Weber, G., et al., (1996) "Tiazofurin: Molecular and clinical action", *Anticancer Research* 16:3313–3322.

Weiss, R.S., et al. (1997) "A caboxy–terminal region required by the adneovirus type 9 E4 ORF1 oncoprotein for transformation mediates direct binding to cellular polypeptides", *J. Virol.* 71(10):7873–7880.

Whitesell, et al., (1991) "Episome–generated N–myc antisense RNA restricts the differentiation potential of primitive neuroectodermal cell lines",*Mol. Cell. Biol.,* 11(3):1360–1371.

Wikstrand, C.J., et al., (1997) "Cell surface localization and density of the tumor–associated variant of the epidermal growth factor receptor, EGFRvIII", *Cancer Research* 57(18):4130–4140.

Woolf, et al., (1990) "The stability, toxicity and effectiveness of unmodified and phosphorothioate antisesne ogligodeoxynucleotides in Xenopus oocytes and embryos", *Nucleic Acids Res.* 18(7):1763–1769.

Wright J. A. et al., (1995) "Antisense molecules and their potential for the treatment of cancer and AIDS", *The Cancer Journal* 8(4):185–189.

Wright, J.A. (1989) "Altered mammalian ribonucleoside diphosphate reductase from mutant cell lines" *Int. Encyclop. Pharmacol. Therapeut.* 128:89–111.

Wright, J.A., et al., (1990 "Regulation and drug resistance mechanisms of mammalian ribonucleotide reductase, and the significance to DNA synthesis", *Biochem. Cell Biol.* 68:1364–1371.

Xie, S., et al., (1997) "Expression of MCAM/MUC18 by human melanoma cells leads to increased tumor growth and metastasis", *Cancer Research* 57(11):2295–2303.

Yakubov, et al., (1989) "Mechanism of oligonucleotide uptake by cells: Involvement of specific receptors?", *Proc. Natl. Acad. Sci. USA* 86:6454–6458.

Yamada, M., et al., (1996) Increased expression of thioredoxin/adult T–cell leukemia–derived factor in Cisplatin–resistant human cancer cell lines', *Clinical Cancer Research* 2:427–432.

Yokomizo, A., et al., (1995) "Cellular levels of thioredoxin associated with drug sensitivity to cisplatin, mitomycin C, doxorubicin, and etoposide", *Cancer Research* 55:4293–4296.

Zauli, G., et al., (1997) "Thrombopoietin enhances the $alpha_{IIb}$ $beta_3$–dependent adhesion of magakaryocyte cells to fibrinogen or fibronectin through PI 3 kinase", *Blood* 89(3):883–895.

* cited by examiner

Overexpression of hTrx in human tumor cell lines
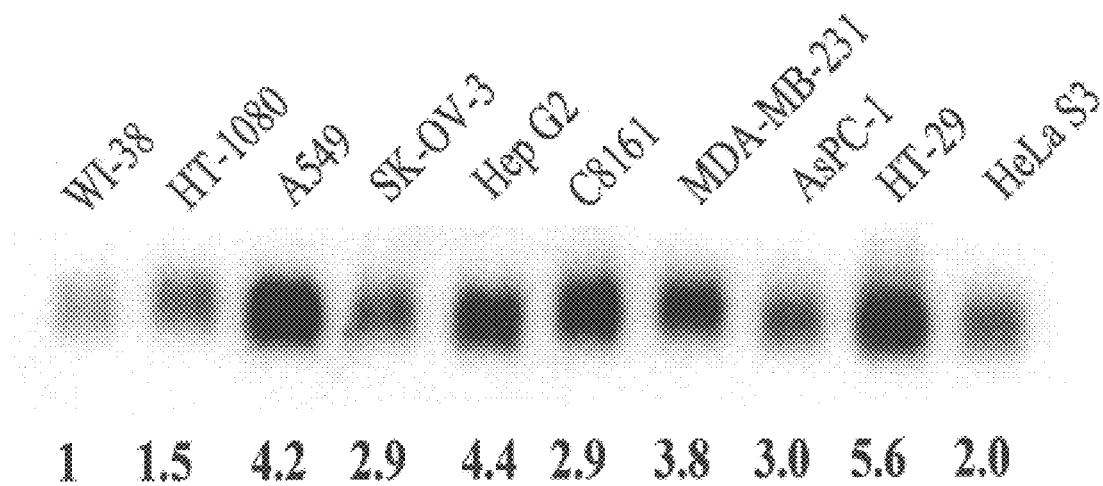
FIG. 1A
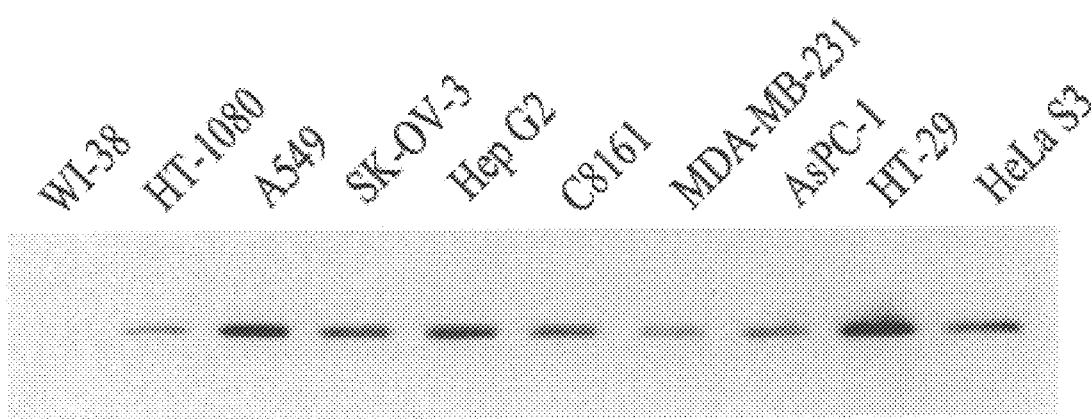
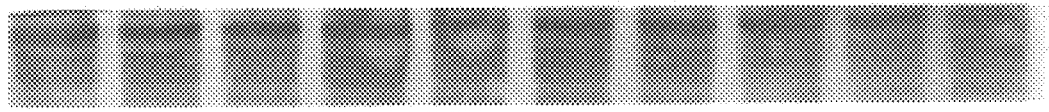
FIG. 1B

```
                                GTI2602              GTI2604
                 GTI2601                  GTI2603
agtcttgaagctctgtttggtgctttggatccatttccatcggtccttacagccgctcgt
              GTI2606
    GTI2605             GTI2607                    GTI2608
cagactccagcagccaagatggtgaagcagatcgagagcaagactgcttttcaggaagcc
                         M  V  K  Q  I  E  S  K  T  A  F  Q  E  A
         GTI2609
                                        GTI2610
ttggacgctgcaggtgataaacttgtagtagttgacttctcagccacgtggtgtgggcct
 L  D  A  A  G  D  K  L  V  V  V  D  F  S  A  T  W  C  G  P
      GTI2612
  GTI2611         GTI2613            GTI2614
tgcaaaatgatcaagcctttctttcattccctctctgaaaagtattccaacgtgatattc
 C  K  M  I  K  P  F  F  H  S  L  S  E  K  Y  S  N  V  I  F
      GTI2615           GTI2616            GTI2617
cttgaagtagatgtggatgactgtcaggatgttgcttcagagtgtgaagtcaaatgcatg
 L  E  V  D  V  D  D  C  Q  D  V  A  S  E  C  E  V  K  C  M
                           GTI2618
ccaacattccagttttttaagaagggacaaaaggtgggtgaattttctggagccaataag
 P  T  F  Q  F  F  K  K  G  Q  K  V  G  E  F  S  G  A  N  K
                                            GTI2621
     GTI2619                      GTI2620
gaaaagcttgaagccaccattaatgaattagtctaatcatgtttctgaaaatataaccag
 E  K  L  E  A  T  I  N  E  L  V  end
               GTI2623
    GTI2622
ccattgagctatttaaaacttgtaattttttttaatttacaaaaatataaaatatgaagac
                 GTI2625
   GTI2624              GTI2626
ataaacccagttgccatctgcgtgacaataaaacattaatgctaacacttttaaaaccg tctcatgtctgaatagctttcaaaataaatgtgaaatggtc
```

FIG. 2 hTrx Protein Levels in Human Colon (HT-29) Tumors

OLIGONUCLEOTIDE SEQUENCES COMPLEMENTARY TO THIOREDOXIN OR THIOREDOXIN REDUCTASE GENES AND METHODS OF USING SAME TO MODULATE CELL GROWTH

REFERENCE TO RELATED APPLICATIONS

This application claims priority to U.S. Provisional Application Ser. No. 60/073,196 filed Jan. 30, 1998, which application is incorporated herein by reference in its entirety.

BACKGROUND OF THE INVENTION

1. Field of the Invention

This invention relates to oligonucleotides that are complementary to the thioredoxin and thioredoxin reductase genes which modulate tumor cell growth in mammals. This invention is also related to methods of using such compounds in inhibiting the growth of tumor cells in mammals. This invention also relates to pharmaceutical compositions comprising a pharmaceutically acceptable excipient and an effective amount of a compound of this invention.

References

The following publications, patent applications and patents are cited in this application as superscript numbers:

1. Holmgren, "Enzymatic reduction-oxidation of protein disulfide by thioredoxin" *Methods Enzymol* 107:295–300 (1984)
2. Wright and Anazodo, "Antisense Molecues and their potential for the treatment of cancer and AIDS" *The Cancer Journal* 4:185–189 (1995)
3. Matthew et al., "Thioredoxin regulates the DNA binding activity of NF-Kappa B by reduction of a disulphide bond involving cysteine 62 *Nucleic Acids Res.* 20:3821–3830 (1992)
4. Bannister et al., "In vitro DNA binding activity of Fos/Jun and BZLF1 but not C/EBP is affected by redox changes" *Oncogene* 6:1243–50 (1991)
5. Cromlish and Roeder "Human transcription factor IIIC (TFIIIC)" *J. Biol. Chem.* 264:18100–9 (1989)
6. Abate et al., "Redox regulation of fos and jun DNA-binding activity in vitro" *Science* 249:1157–1161 (1990)
7. Tagaya et al., "ATL-derived factor (ADF), an IL-2 receptor/Tac inducer homologous to thioredoxin: possible involvement of dithiol-reduction in the Il-2 receptor induction *EMBO J.* 8:757–64 (1989)
8. Powis et al., "The thioredoxin/thioredoxin reductase redox system and control of cell growth" *Oncol. Res.* 6:53944 (1994)
9. Oblong et al., "Site directed mutagenesis of active site cysteines in human thioredoxin produces competitive inhibitors of human thioredoxin reductase and elimination of mitogenic properties of thioredoxin *J. Biol. Chem.* 269:11714–20 (1994)
10. Gasdaska et al. "Cell growth stimulation by the redox protein thioredoxin occurs by a novel helper mechanism" *Cell Growth Differ* 6:1643–1650 (1995)
11. Gasdaska et al., "The predicted amino acid sequence of human thioredoxin is identical to that of the autocrine growth factor human adult T-cell derived factor (ADF); thioredoxin mRNA is elevated in some human tumors" *Biochem Biophys. Acta* 1218:292–296 (1994)
12. Berggren et al., "Thioredoxin and thioredoxin reductase gene expression in human tumors and cell lines and the effects of serum stimulation and hypoxia" *Anticancer Res.* 16:3459–3466 (1996)
13. Fujii et al., "Coexpression of adult T-cell leukemia-derived factor, a human thioredoxin homologue and human papillomavirus DNA in neoplastic cervical squamous epithelium" *Cancer* 68:1583–91 (1991)
14. Kawahara et al., "Enhanced coexpression of thioredoxin and high mobility group protein 1 genes in human hepatocellular carcinoma and the possible association with decreased sensitivity to cisplatin" *Cancer Res.* 56:5330–3 (1996)
15. Gallegos et al., "Transfection with human thioredoxin increases cell proliferation and a dominant-negative mutant thioredoxin reverses the transformed phenotype of human breast cancer cells", *Cancer Res.* 56:5765–70 (1996)
16. Baker et al., "Thioredoxin, a gene found overexpressed in human cancer, inhibits apoptosis in vitro and in vivo" *Cancer Res.* 57:5162–7 (1997)
17. Mau and Powis, "Inhibition of cellular thioredoxin reductase by diaziquinone and doxorubicin. Relationship to the inhibition of cell proliferation and decreased ribonucleotide reductase activity" *Biochem Pharmacol* 43: 1621–7 (1992)
18. Mau and Powis, "Mechanism-based inhibition of thioredoxin reductase by antitumor quinoid compounds" *Biochem Pharmacol* 43: 1613–20 (1992)
19. Schallreuter and Wood, "New aspects in the pathophysiology of cutaneous melanoma: a review of the role of thioproteins and the effect to nitrosoureas" *Melanoma Res.* 1:159–167 (1991)
20. Schallreuter and Wood, "The stereospecific suicide inhibition of human melanoma thioredoxin reductase by 13-cis-retinoic acid" *Biochem Biophys. Res. Commun.* 160:573–9 (1989)
21. Curcio et al., "Oligonucleotides as modulators of cancer gene expression" *Pharmacol Ther.* 74:317–32 (1997)
22. Narayanan and Akhtar, "Antisense therapy" *Curr Opin. Oncol.* 8:509–15 (1996)
23. Remington's Pharmaceutical Sciences, Mace Publishing Company, Philadelphia, Pa. 17$^{th}$ ed. (1985)
24. Sambrook et al., *Molecular Cloning: A Laboratory Manual*, Cold Spring Harbor Laboratory, New York (1989, 1992)
25. Ausubel et al., *Current Protocols in Molecular Biology*, John Wiley and Sons, Baltimore, Md. (1989)
26. Perbal, *A Practical Guide to Molecular Cloning*, John Wiley & Sons, New York (1988)
27. Hurta and Wright, "Malignant transformation by H-ras results in aberrant regulation of ribonucleotide reductase gene expression by transforming growth factor-beta" *J. Cell Biochem* 57:543–556 (1995)
28. Tagaya et al., "ATL-derived factor (ADF) an IL-2-receptor/Tac inducer homologous to thioredoxin: possible involvement of dithiol-reduction in the IL-2 receptor induction" *EMBO J.* 13:2244 (1994)
29 Choy et al., "Molecular mechanisms of drug resistance involving ribonucleotide reductase: hydroxyurea resistance in a series of clonally related mouse cell lines selected in the presence of increasing drug concentrations" *Cancer Res.* 48:2029–2035 (1988)
30. Fan et al., "Ribonucleotide reductase R2 component is a novel malignancy determinant that cooperates with activated oncogenes to determine transformation and malignant potential" *Proc. Natl. Acad. Sci USA* 93:14036–40 (1996)
31. Huang and Wright, "Fibroblast growth factor mediated alterations in drug resistance and evidence of gene amplification" *Oncogene* 9:491499 (1994)

32. Gasdaska et al., "Cloning and sequencing of a human thioredoxin reductase" *FEBS Letters* 373:5–9 (1995)
29. Nielsen et al.; *Science* (1991) 354:1497
30. Good and Nielsen; "Inhibition of translation and bacterial growth by peptide nucleic acid targeted to ribosomal RNA", *PNAS USA* (1998) 95:2073–2076
31. Buchardt, deceased, et al., U.S. Pat. No. 5,766,855
32. Buchardt, deceased, et al., U.S. Pat. No. 5,719,262
33. U.S. Pat. No. 5,034,506[33]
34. Altschul, et al. "Basic local alignment search tool", *J. Mol. Biol.* (1990) 215:403–10;
35. Devereux J. et al., "A comprehensive set of sequence analysis programs for the VAX", *Nucleic Acids Res.* (1984) 12:387–395;
36. Chang et al.[36]; Somatic Gene Therapy, CRC Press, Ann Arbor, Mich. (1995);
37. Vega et al.[37]; Gene Targeting, CRC Press, Ann Arbor, Mich. (1995)
38. *Vectors: A Survey of Molecular Cloning Vectors and Their Uses*, Butterworths, Boston, Mass. (1988)
39. Sullivan 1994, U.S. Pat. No. 5,225,347
40. U.S. Pat. No. 5,023,252 issued Jun. 11, 1991
41. Felgner et al., U.S. Pat. No. 5,580,859
42. U.S. Pat. No. 5,011,472
43. Dreeley et al., Science, 258:1650–1654 (1992)

All of the above publications, patent applications and patents are herein incorporated by reference in their entirety to the same extent as if each individual publication, patent application or patent was specifically and individually indicated to be incorporated by reference in its entirety.

2. State of the Art

Thioredoxin is a small ubiquitous redox protein originally identified as a reducing cofactor for ribonucleotide reductase which is essential for DNA synthesis[1]. Thioredoxin and thioredoxin reductase comprise the thioredoxin system. Thioredoxin reductase is a selenocysteine containing flavoenzyme which uses NADPH as a proton donor to reduce thioredoxin which in turn reduces other proteins and therefore influences their functions.

In recent years, mammalian thioredoxin has been implicated in a variety of other biochemical pathways. For example, it modulates redox properties of transcription factors by dithiol disulfide exchanges, which alter their DNA binding characteristics. Transcription factors such as NF-κB[3], BZLFI[4] and TFIIIC[5] are directly regulated, while AP-1 activation is mediated indirectly through the nuclear redox factor Ref-1 which is further reduced by thioredoxin[6]. In addition, thioredoxin has been shown to facilitate refolding of disulfide-containing proteins, to activate the glucocorticoid or interleukin-2-receptors, to inhibit human immunodeficiency virus expression in macrophages, to reduce $H_2O_2$ scavenge free radicals, to protect cells against oxidative stress and to be an early pregnancy factor.

Cloned human thioredoxin has been shown to be similar to a growth factor termed adult T-cell leukemia-derived factor, released by HTLV-1 transformed T cells[7]. It utilizes a pathway for secretion. Extracellularly expressed thioredoxin stimulates the proliferation of normal fibroblasts, lymphoid cells and a number of human solid tumor cell lines[8 & 9]. Redox-inactive forms have been used to show that the growth stimulation requires a redox activity of thioredoxin[9]. The growth stimulation by thioredoxin appears to be induced indirectly through sensitizing cells to other growth factors[10]. Subsequently, thioredoxin has been reported to be over-expressed in some primary tumors such as lung, colon, cervical and hepatocellular carcinoma[11-14]. Furthermore, human breast cancer cells transfected with wild-type thioredoxin cDNA have shown increased tumor growth[15], decreased spontaneous apoptosis in vivo[16] and decreased sensitivity to apoptosis induced by a variety of anticancer therapeutic compounds[16]. On the other hand, cells transfected with dominant-negative, redox-inactive mutant thioredoxin have shown reduced anchorage-independent growth in vitro and inhibition of tumor growth in vivo[15].

Thioredoxin reductase has been shown to be overexpressed by a number of human tumors[12]. Inhibition of cellular thioredoxin reductase by antitumor quinones[17 & 18], nitrosoureas[19] and 13-cis-retinoic acid[20] have led to a decreased activity of the thioredoxin system and consequent contribution to the growth inhibitory activity.

Antisense oligonucleotides have been utilized to inhibit gene expression in a target-specific manner by sequence-specific hybridization to target mRNA[2]. Antisense oligonucleotide-mediated repression of oncogenes has revealed that these compounds may be useful for identifying mechanisms governing oncogenesis[21] and may also be promising as novel therapeutic compounds for the treatment of cancer[22]. Therefore, it would be desirable to identify antisense oligonucleotides directed against thioredoxin and thioredoxin reductase which act to inhibit the expression of thioredoxin or thioredoxin reductase with higher specificity and with less toxicity.

SUMMARY OF THE INVENTION

This invention is directed to antisense oligonucleotides which modulate the expression of the thioredoxin and ihioredoxin reductase genes in tumor cells in mammals and pharmaceutical compositions comprising such antisense oligonucleotides. This invention is also related to methods of using such antisense oligonucleotides for inhibiting the growth and metastasis of tumor cells in mammals.

Accordingly, in one of its composition aspects, this invention is directed to an antisense oligonucleotide, which oligonucleotide comprises from about 3 to about 50 nucleotides, which nucleotides are complementary to the thioredoxin mRNA or the thioredoxin reductase mRNA of a mammal. The antisense oligonucleotide may be nuclease resistant and may have one or more phosphorothioate internucleotide linkages. The antisense oligonucleotide may further comprise additional nucleotides which are not complementary to the thioredoxin mRNA or the thioredoxin reductase mRNA.

In another of its composition aspects, this invention is directed to an antisense oligonucleotide comprising from about 17 to about 50 nucleotides, wherein the oligonucleotide comprises a sequence selected from the group consisting of sequences 2601–2626 [SEQ ID NOs:1–26] as set forth in Table 1.

In another of its composition aspects, this invention is directed to an antisense oligonucleotide comprising from about 20 to about 50 nucleotides, wherein the oligonucleotide comprises a sequence selected from the group consisting of sequences 3001–3040 [SEQ ID NOs:27–66] as set forth in Table 2.

In still another of its composition aspects, this invention is directed to a pharmaceutical composition comprising a pharmaceutically acceptable excipient and an effective amount of an antisense oligonucleotide, which oligonucleotide comprises from about 3 to about 50 nucleotides, which nucleotides are complementary to the thioredoxin gene or the thioredoxin reductase gene of a mammal.

In still another of its composition aspects, this invention is directed to a pharmaceutical composition comprising a pharmaceutically acceptable excipient and an effective amount of an antisense oligonucleotide comprising from about 17 to about 50 nucleotides, wherein the oligonucleotide comprises a sequence selected from the group consisting of sequences 2601–2626 [SEQ ID NOs:1–26] as set forth in Table 1.

In still another of its composition aspects, this invention is directed to a pharmaceutical composition comprising a pharmaceutically acceptable excipient and an effective amount of an antisense oligonucleotide comprising from about 20 to about 50 nucleotides, wherein the oligonucleotide comprises a sequence selected from the group consisting of sequences 3001–3040 [SEQ ID NOs:27–66] as set forth in Table 2.

In one of its method aspects, this invention is directed to a method for inhibiting the growth of a mammalian tumor comprising, administering to a mammal suspected of having the tumor an effective amount of an antisense oligonucleotide comprising from about 3 nucleotides to about 50 nucleotides complementary to the thioredoxin gene of the mammal under conditions such that the growth of the tumor is inhibited. The antisense oligonucleotide may be administered with a chemotherapeutic agent.

In another of its method aspects, this invention is directed to a method for inhibiting the growth of a mammalian tumor comprising, administering to a mammal suspected of having the tumor an effective amount of an antisense oligonucleotide comprising from about 3 nucleotides to about 50 nucleotides complementary to the thioredoxin reductase gene of the mammal under conditions such that the growth of the tumor is inhibited. The antisense oligonucleotide may be administered with a chemotherapeutic agent.

In another of its method aspects, this invention is directed to a method for inhibiting the metastasis of a mammalian tumor comprising, administering to a mammal suspected of having a metastatic tumor an effective amount of an antisense oligonucleotide comprising from about 3 nucleotides to about 50 nucleotides complementary to the thioredoxin gene of the mammal under conditions such that the metastasis of the tumor is inhibited. The antisense oligonucleotide may be administered with a chemotherapeutic agent.

In another of its method aspects, this invention is directed to a method for inhibiting the metastasis of a mammalian tumor comprising, administering to a mammal suspected of having the tumor an effective amount of an antisense oligonucleotide comprising from about 3 nucleotides to about 50 nucleotides complementary to the thioredoxin reductase gene of the mammal under conditions such that the metastasis of the tumor is inhibited. The antisense oligonucleotide may be administered with a chemotherapeutic agent.

BRIEF DESCRIPTION OF THE DRAWINGS

FIG. 1A is an autoradiograph of a Northern blot of thioredoxin mRNA in various cell lines: Human normal embryonic lung cell line (WI-38), fibrosarcoma (HT-1080), lung carcinoma (A549), ovary adenocarcinoma (SK-OV-3), hepatocellular carcinoma (Hep G2), melanoma (C8161) breast adenocarcinoma (MDA-MB-231), metastatic pancreatic adenocarcinoma (AsPC-1), colon adenocarcinoma (HT-29), cervical carcinoma (HeLa S3).

FIG. 1B is a photograph of a Western blot of thioredoxin protein expressed in various cell lines. The lower panel shows the total protein loaded in each lane.

FIG. 2 is the cDNA sequence of thioredoxin [SEQ ID NOs: 67 and 68]. The hybridization sites to which the 26 different antisense oligonucleotides anneal is indicated.

FIG. 9A is the human colon cancer cell line HT-29 and FIG. 9B is the human breast cancer cell line MDA-MB-231.

DETAILED DESCRIPTION OF THE INVENTION

Definitions

Figure 3A:
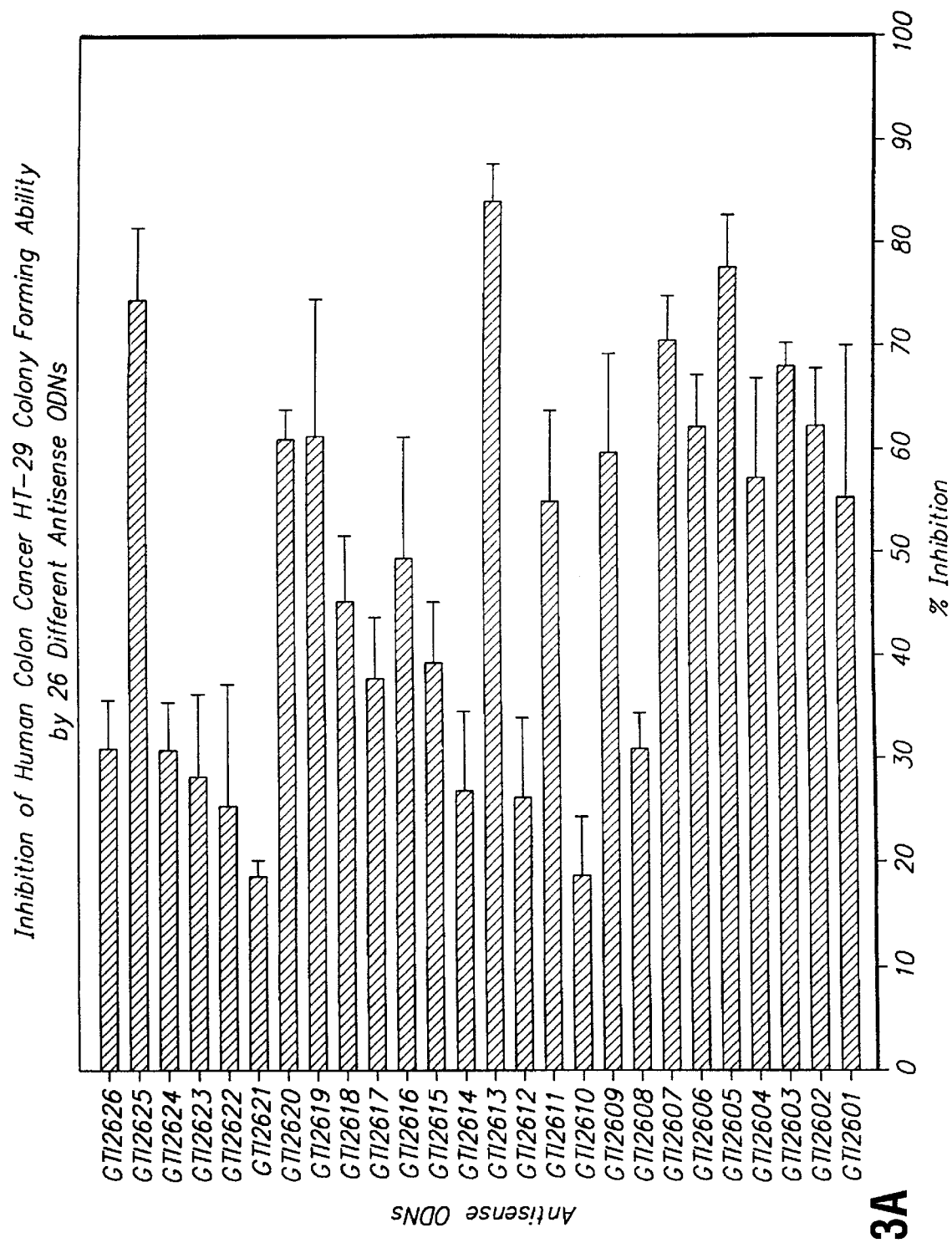
FIGS. 3A–3F are graphs showing the percentage inhibition of various human cancer cell line's colony forming ability after treatment with 26 different antisense oligonucleotides complementary to the thioredoxin cDNA. The cell lines tested were human colon cancer HT-29 (FIG. 3A), human breast cancer cell line MDA-MB-231(FIG. 3B), human liver cancer cell line HepG2 (FIG. 3C), human melanoma cell line A2058 (FIG. 3D), human ovary cancer cell line SK-OV-3 (FIG. 3E) and human lung cancer cell line A549 (FIG. 3F).

As used herein, the following terms have the following meanings:

The term "antisense oligonucleotide" as used herein means a nucleotide sequence that is complementary to the desired mRNA. Preferably, the antisense oligonucleotide is complementary to the thioredoxin mRNA or the thioredoxin reductase mRNA. It is contemplated that the antisense oligonucleotide may be complementary to any of the 5' untranslated region of the mRNA, the coding region or the 3' untranslated region of the mRNA.

The term "oligonucleotide" refers to an oligomer or polymer of nucleotide or nucleoside monomers consisting of naturally occurring bases, sugars, and intersugar (backbone) linkages. The term also includes modified or substituted oligomers comprising non-naturally occurring monomers or portions thereof, which function similarly. Such modified or substituted oligomers may be preferred over naturally occurring forms because of the properties such as enhanced cellular uptake, or increased stability in the presence of nucleases. The term also includes chimeric oligonucleotides which contain two or more chemically distinct regions. For example, chimeric oligonucleotides may contain at least one region of modified nucleotides that confer beneficial properties (e.g. increased nuclease resistance, increased uptake into cells) or two or more oligonucleotides of the invention may be joined to form a chimeric oligonucleotide.

The antisense oligonucleotides of the present invention may be ribonucleic or deoxyribonucleic acids and may contain naturally occurring or synthetic monomeric bases, including adenine, guanine, cytosine, thymine and uracil. The oligonucleotides may also contain modified bases such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thioalkyl guanines, 8-hydroxyl guanine and other 8-substituted guanines, other aza and deaza uracils, thymidines, cytosines or guanines, 5-trifluoromethyl uracil and 5-trifluoro cytosine. The modifications may also include attachment of other chemical groups such as methyl, ethyl, propyl groups to the various parts of the oligonucleotides including the sugar, base or backbone components.

The antisense oligonucleotides of the invention may also comprise modified phosphorus oxygen heteroatoms in the phosphate backbone, short chain alkyl or cycloalkyl intersugar linkages or short chain heteroatom or heterocyclic intersugar linkages. For example, the antisense oligonucleotides may contain methyl phosphonates, phosphorothioates, phosphorodithioates, phosphotriesters, and morpholino oligomers. In one embodiment of the invention, the antisense oligonucleotides comprise phosphorothioate bonds linking between the four to six 3'-terminus nucleotides. In another embodiment, the phosphorothioate bonds link all the nucleotides. The antisense oligonucleotides may also have sugar mimetics.

The antisense oligonucleotides of the invention may also comprise nucleotide analogues wherein the structure of the nucleotide is fundamentally altered. An example of such an oligonucleotide analogue is a peptide nucleic acid (PNA) wherein the deoxyribose (or ribose) phosphate backbone in DNA (or RNA) is replaced with a polyamide backbone which is similar to that found in peptides (Nielsen et al.[29]; Good and Nielsen[30]; Buchardt, deceased, et al.[31], U.S. Pat. No. 5,766,855; Buchardt, deceased, et al.[32], U.S. Pat. No. 5,719,262). PNA analogues have been shown to be resistant to degradation by enzymes and to have extended lives in vivo and in vitro. PNAs also bind more strongly to a complementary DNA sequence than to a naturally occurring nucleic acid molecule due to the lack of charge repulsion between the PNA strand and the DNA strand.

The oligonucleotides of the present invention may also include other nucleotides comprising polymer backbones, cyclic backbones, or acyclic backbones. For example, the nucleotides may comprise morpholino backbone structures (U.S. Pat. No. 5,034,506[33]).

The oligonucleotides of the present invention are "nuclease resistant" when they have either been modified such that they are not susceptible to degradation by DNA and RNA nucleases or alternatively they have been placed in a delivery vehicle which in itself protects the oligonucleotide from DNA or RNA nucleases. Nuclease resistant oligonucleotides include, for example, methyl phosphonates, phosphorothioates, phosphorodithioates, phosphotriesters, and morpholino oligomers. Suitable delivery vehicles for conferring nuclease resistance include, for example liposomes.

The oligonucleotides of the present invention may also contain groups, such as groups for improving the pharmacokinetic properties of an oligonucleotides, or groups for improving the pharmacodynamic properties of an oligonucleotide. Preferably, the oligonucleotides do not contain reporter groups or labels, such as fluorescent dyes or radioactive labels.

The antisense oligonucleotides are preferably selected from the sequence complementary to the thioredoxin or thioredoxin reductase genes such that the sequence exhibits the least likelihood of showing duplex formation, hair-pin formation, and homooligomer/sequence repeats but has a high to moderate potential to bind to the thioredoxin or thioredoxin reductase gene sequences. These properties may be determined using the computer modeling program OLIGO Primer Analysis Software, Version 5.0 (distributed by National Biosciences, Inc., Plymouth, Minn.). This computer program allows the determination of a qualitative estimation of these five parameters.

Alternatively, the antisense oligonucleotides may also be selected on the basis that the sequence is highly conserved for either the thioredoxin or thioredoxin reductase gene between two or more mammalian species. These properties may be determined using the BLASTN program (Altschul, et al.[34]) of the University of Wisconsin Computer group (GCG) software (Devereux J. et al.[35]) with the National Center for Biotechnology Information (NCBI) databases.

The antisense oligonucleotides may include mutations, such as substitutions, insertions and deletions. Preferably there will be less that 10% of the sequence having mutations.

The antisense oligonucleotides generally comprise from at least about 3 nucleotides or nucleotide analogs, preferably from about 3 to about 100 nucleotides or nucleotide analogs, more preferably, from about 3 to about 50 nucleotides or nucleotide analogs, most preferably from about 17 to about 35 nucleotide or nucleotide analogs.

Preferably, the antisense oligonucleotides comprise the sequences set forth in Tables 1 and 2 (below).

TABLE 1

Antisense oligonucleotides having a sequence complementary to the human thioredoxin mRNA

| SEQ ID No: | Name | Sequence 5'→3' | Tm (° C.) | ΔG (kcal/mol) |
|---|---|---|---|---|
| 1 | 2601 | TCC AAA GCA CCA AAC AGA GC | 61.9 | -38.2 |
| 2 | 2602 | GAT GGA AAT GGA TCC AA | 50.7 | -31.6 |
| 3 | 2603 | TAA GGA CCG ATG GAA ATG GA | 61.2 | -38.8 |
| 4 | 2604 | GAC GAG CGG CTG TAA GGA CC | 65.4 | -41.0 |
| 5 | 2605 | TTG GCT GCT GGA GTC TGA CG | 65.2 | -39.3 |
| 6 | 2606 | GCT TCA CCA TCT TGG CTG CT | 63.5 | -39.3 |
| 7 | 2607 | GCT CTC GAT CTG CTT CAC CA | 61.7 | -37.7 |
| 8 | 2608 | GCG TCC AAG GCT TCC TGA AA | 66.0 | -41.4 |
| 9 | 2609 | GTT TAT CAC CTG CAG CGT CC | 61.4 | -38.3 |
| 10 | 2610 | ACG TGG CTG AGA AGT CAA CT | 57.7 | -35.7 |
| 11 | 2611 | GAT CAT TTT GCA AGG CCC AC | 63.7 | -39.8 |
| 12 | 2612 | GGC TTG ATC ATT TTG CAA GG | 61.7 | -38.9 |
| 13 | 2613 | AGG GAA TGA AAG AAA GGC TT | 58.7 | -38.4 |
| 14 | 2614 | TCA CGT TGG AAT ACT TTT CA | 54.7 | -34.7 |
| 15 | 2615 | CAT CCA CAT CTA CTT CAA GG | 53.2 | -33.8 |
| 16 | 2616 | TCT GAA GCA ACA TCC TGA CA | 57.4 | -34.8 |
| 17 | 2617 | GGCATG CAT TTG ACT TCA CA | 60.7 | -36.8 |
| 18 | 2618 | TCA CCC ACC TTT TGT CCC TT | 62.5 | -39.1 |
| 19 | 2619 | GGC TTC AAG CTT TTC CTT | 55.4 | -35.3 |
| 20 | 2620 | ATA TTT TCA GAA ACA TGA TT | 47.3 | -31.8 |
| 21 | 2621 | CAA TGG CTG GTT ATA TTT TC | 53.9 | -35.5 |
| 22 | 2622 | GTT TTA AAT AGC TCA ATG GC | 53.6 | -35.6 |
| 23 | 2623 | TTA AAA AAA TTA CAA GTT TT | 46.7 | -32.4 |
| 24 | 2624 | GCA ACT GCT GGG TTT ATG TCT TC | 55.5 | -35.4 |
| 25 | 2625 | TCA CGC AGA TGG CAA CTG GG | 68.2 | -41.0 |
| 26 | 2626 | GTT TTA TTG TCA CGC AGA TG | 54.7 | -34.6 |

TABLE 2

Antisense oligonucleotides complementary to the sequence of the human thioredoxin reductase mRNA

| SEQ ID No: | Name | Sequence 5'→3' | Tm (° C.) | ΔG (kcal/mol) |
|---|---|---|---|---|
| 27 | 3001 | CCC GAC GCA GAG CTT ACA AG | 64.4 | -40.4 |
| 28 | 3002 | GCT CGC GGC TTT GTC TGG TT | 68.4 | -42.8 |
| 29 | 3003 | CCG TCC CCA GCG TGC TCC CA | 80.0 | -49.9 |
| 30 | 3004 | GCT GTC GTC CCC GCC GGC AG | 77.9 | -48.4 |
| 31 | 3005 | CTG CTG CAC CCA GGC GCA AT | 72.1 | -44.3 |
| 32 | 3006 | TCT TCC CTT CCC CGA GAC GC | 69.4 | -43.7 |
| 33 | 3007 | CCG TCT GCT CAG ACA CGC CT | 66.7 | -40.4 |
| 34 | 3008 | CCG CAC ACG CCA CGA AGC TG | 73.5 | -44.5 |
| 35 | 3009 | GAA GCT TTG TGT GAC CGG GT | 63.1 | -39.0 |
| 36 | 3010 | TCA GGG CCC GAC CGT CCT CA | 73.5 | -44.9 |
| 37 | 3011 | GCA GAT CGG TTT CCG CGG CC | 74.8 | -47.4 |
| 38 | 3012 | GGT TGG ACC ATG GCC GCC TA | 70.8 | -44.3 |
| 39 | 3013 | AGG GCC GTT CAT TTT TAG TA | 58.2 | -38.3 |
| 40 | 3014 | AGA TCT TCA GGG CCG TTC AT | 61.9 | -39.1 |
| 41 | 3015 | AGC AGC TGC CAG ACC TCC TG | 65.9 | -40.3 |
| 42 | 3016 | CAA GAG GGG TGG GAG TGA CA | 63.5 | -38.5 |
| 43 | 3017 | TTT CGA GAG TCT TGC AGG GC | 63.7 | -39.6 |
| 44 | 3018 | CTC GGT AGC CCC AAT TCA AA | 63.6 | -40.7 |
| 45 | 3019 | TTG TCA CCA GGG ATG CCC AA | 67.4 | -40.8 |
| 46 | 3020 | TCC AAA GCG ACA TAG GAT GC | 61.9 | -38.8 |
| 47 | 3021 | CCT ATT GCC AGC ATC ACC GT | 64.2 | -40.0 |
| 48 | 3022 | CTG GAT TGC AAC TGG GGT GA | 64.6 | -39.3 |
| 49 | 3023 | CCT CAG AAA GGC CAC AAG CA | 64.4 | -39.7 |
| 50 | 3024 | TTG AGC GCA GCT GCA AGG CC | 70.5 | -43.5 |
| 51 | 3025 | GAG CGC TTG GTC ACA GAC AA | 62.6 | -37.8 |
| 52 | 3026 | AAC AGC ATC CAC ACT GGG GC | 66.1 | -40.2 |
| 53 | 3027 | GCA CGG AAA CGA GCC AGT GG | 69.3 | -42.5 |
| 54 | 3028 | ACG CAG GTG CCA AGA GCC CA | 71.6 | -43.8 |
| 55 | 3029 | GTG ACC CCA GTG TGA TGC TG | 62.1 | -36.9 |
| 56 | 3030 | TCG ATG CCC TGC CAA ATG TC | 67.2 | -41.2 |
| 57 | 3031 | ACA GTT GTT CCA TCA CCG CC | 63.7 | -38.9 |
| 58 | 3032 | TCC CTT CCA TGC AAC AAG AC | 61.4 | -37.8 |
| 59 | 3033 | TTT CCC GGG ACA AGC CTA CA | 66.2 | -41.7 |
| 60 | 3034 | GCA CAC AGG GGC AAA TTT GG | 66.8 | -41.4 |
| 61 | 3035 | CTA CCA AAT GCC AGG CAA TG | 62.4 | -39.2 |
| 62 | 3036 | TGT TTC TCC CCC ATT TCT GG | 63.1 | -39.6 |
| 63 | 3037 | GTT CCC TGA GGT GGC CCA GA | 67.6 | -41.5 |
| 64 | 3038 | ACG GTC AGG GGC TCT GCT GC | 70.4 | -43.2 |
| 65 | 3039 | ATG AGG ACG TGA GGC AGA GC | 63.1 | -38.6 |
| 66 | 3040 | TGG TCA ACT GCC TCA ATT GC | 62.5 | -38.1 |

In Tables 1 and 2 the "Tm" is the melting temperature of an oligonucleotide duplex calculated according to the nearest-neighbour thermodynamic values. At this temperature 50% of nucleic acid molecules are in duplex and 50% are denatured. The "ΔG" is the free energy of the oligonucleotide, which is a measurement of an oligonucleotide duplex stability.

The term "alkyl" refers to monovalent alkyl groups preferably having from 1 to 20 carbon atoms and more preferably 1 to 6 carbon atoms. This term is exemplified by groups such as methyl, ethyl, n-propyl, iso-propyl, n-butyl, iso-butyl, n-hexyl, and the like.

The term "aryl" refers to an unsaturated aromatic carbocyclic group of from 6 to 14 carbon atoms having a single ring (e.g., phenyl) or multiple condensed (fused) rings (e.g., naphthyl or anthryl). Preferred aryls include phenyl, naphthyl and the like.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The term "halo" or "halogen" refers to fluoro, chloro, bromo and iodo and preferably is either fluoro or chloro.

The term "thiol" refers to the group —SH.

As to any of the above groups which contain one or more substituents, it is understood, of course, that such groups do not contain any substitution or substitution patterns which are sterically impractical and/or synthetically non-feasible. In addition, the compounds of this invention include all stereochemical isomers arising from the substitution of these compounds.

The term "pharmaceutically acceptable salt" refers to salts which retain the biological effectiveness and properties of the antisense oligonucleotides of this invention and which are not biologically or otherwise undesirable. In many cases, the antisense oligonucleotides of this invention are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri (cycloalkyl) amines, substituted cycloalkyl amines, disubstituted cycloalkyl amine, trisubstituted cycloalkyl amines, cycloalkenyl amines, di(cycloalkenyl) amines, tri (cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Examples of suitable amines include, by way of example only, isopropylamine, trimethylamine, diethylamine, tri(isopropyl)amine, tri(n-propyl)amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnarnic acid, mandelic acid, methanesulfonic acid, ethanesulfonic acid, p-toluene-sulfonic acid, salicylic acid, and the like.

The term "thioredoxin gene" refers to any gene which encodes a protein that is capable of acting as a hydrogen donor for ribonucleotide reductase or methionine sulfoxide reductase. Preferably the thioredoxin gene encodes a protein capable of modulating the redox properties of transcription factors such as NF-κB, BZLF1, TFIIIC and AP-1 and alters their DNA binding characteristics. Other functions which the protein may have, include but are not limited to the ability to facilitate refolding of disulfide containing proteins, to activate glucocorticoid or interleukin-2 receptors, or to inhibit immunodeficiency virus expression in macrophages, to reduce intracellular $H_2O$, to scavenge free radicals, to protect cells against oxidative stress and to act as an essential component of the early pregnancy factor. Preferably, the thioredoxin gene encodes a protein which is capable of stimulating the proliferation of normal fibroblasts, lymphoid cells, and a number of human solid tumor cell lines and is capable of stimulating tumor growth and decreasing apoptosis when overexpressed in human tumors.

The term "thioredoxin reductase gene" refers to any gene which encodes a protein that is capable of catalyzing NADPH-dependent reduction of thioredoxin.

The term "complementary to" means that the antisense oligonucleotide sequence is capable of binding to the target sequence, ie the thioredoxin gene (or mRNA) or the thioredoxin reductase gene (or mRNA). Preferably the antisense oligonucleotide sequence has at least about 75% identity with the target sequence, preferably at least about 90% identity and most preferably at least about 95% identity with the target sequence allowing for gaps or mismatches of several bases. Identity can be determined, for example, by using the BLASTN program of the University of Wisconsin Computer Group (GCG) software. Preferably the antisense oligonucleotide sequence hybridizes to the thioredoxin or thioredoxin reductase mRNA with a melting temperature of at least 45° C., more preferably at least about 50° C. and most preferably at least about 55° C. as determined by the OLIGO program described herein.

The term "inhibiting growth" means a reduction in the growth of at least one tumor cell type by at least 10%, more preferably of at least 50% and most preferably of at least 75%. The reduction in growth can be determined for tumor cells by measuring the size of the tumor in nude mice or the inability of the tumor cells to form colonies in vitro.

The term "mammal" or "mammalian" means all mammals including humans, ovines, bovines, equines, swine, canines, felines and mice, etc.

A "mammal suspected of having a tumor" means that the mammal may have a proliferative disorder or tumor or has been diagnosed with a proliferative disorder or tumor or has been previously diagnosed with a proliferative disorder or tumor, the tumor has been surgically removed and the mammal is suspected of harboring some residual tumor cells.

Preparation of the Antisense Oligonucleotides

The antisense oligonucleotides of the present invention may be prepared by conventional and well-known techniques. For example, the oligonucleotides may be prepared using solid-phase synthesis and in particular using commercially available equipment such as the equipment available from Applied Biosystems Canada Inc., Mississauga, Canada. The oligonucleotides may also be prepared by enzymatic digestion of the naturally occurring thioredoxin or thioredoxin reductase gene by methods known in the art.

Isolation and Purification of the Antisense Oligonucleotides

Isolation and purification of the antisense oligonucleotides described herein can be effected, if desired, by any suitable separation or purification such as, for example, filtration, extraction, crystallization, column chromatography, thin-layer chromatography, thick-layer chromatography, preparative low or high-pressure liquid chromatography or a combination of these procedures. However, other equivalent separation or isolation procedures could, of course, also be used.

An expression vector comprising the antisense oligonucleotide sequence may be constructed having regard to the sequence of the oligonucleotide and using procedures known in the art.

Vectors can be constructed by those skilled in the art to contain all the expression elements required to achieve the desired transcription of the antisense oligonucleotide sequences. Therefore, the invention provides vectors comprising a transcription control sequence operatively linked to a sequence which encodes an antisense oligonucleotide. Suitable transcription and translation elements may be derived from a variety of sources, including bacterial, fungal, viral, mammalian or insect genes. Selection of appropriate elements is dependent on the host cell chosen.

Reporter genes may be included in the vector. Suitable reporter genes include β-galactosidase (e.g. lacZ), chloramphenicol, acetyl-transferase, firefly luciferase, or an immunoglobulin or portion thereof. Transcription of the antisense oligonucleotide may be monitored by monitoring for the expression of the reporter gene.

The vectors can be introduced into cells or tissues by any one of a variety of known methods within the art. Such methods can be found generally described in Sambrook et al.[24]; Ausubel et al.[25]; Chang et al.[36]; Vega et al.[37]; and Vectors: A Survey of Molecular Cloning Vectors and Their Uses[38] and include, for example, stable or transient transfection, lipofection, electroporation and infection with recombinant viral vectors.

Introduction of nucleic acids by infection offers several advantages. Higher efficiency and specificity for tissue type can be obtained. Viruses typically infect and propagate in specific cell types. Thus, the virus' specificity may be used to target the vector to specific cell types in vivo or within a tissue or mixed culture of cells. Viral vectors can also be modified with specific receptors or ligands to alter target specificity through receptor mediated events.

The oligonucleotide of the invention may be insolubilized. For example, the oligonucleotide may be bound to a suitable carrier. Examples of suitable carriers are agarose, cellulose, dextran, Sephadex, Sepharose, carboxymethyl cellulose polystyrene, filter paper, ion-exchange resin, plastic film, plastic tube, glass beads, polyamine-methyl vinyl-ether-maleic acid copolymer, amino acid copolymer, ethylene-maleic acid copolymer, nylon, silk etc. The carrier may in the shape of, for example, a tube, test plate, beads disc, sphere etc.

The insoubilized oligonucleotide may be prepared by reacting the material with the suitable insoluble carrier using known chemical or physical methods, for example, cyanogen bromide coupling.

It is contemplated that the oligonucleotide of this invention may be a ribozyme which cleaves the mRNA. The ribozyme preferably has a sequence homologous to a sequence of an oligonucleotide of the invention and the necessary catalytic center for cleaving the mRNA. For example, a homologous ribozyme sequence may be selected which destroys the thioredoxin or thioredoxin reductase mRNA. The ribozyme type utilized in the present invention may be selected from types known in the art. Several ribozyme structural families have been identified including Group I introns, RNase P, the hepatitis delta virus ribozyme, hammerhead ribozymes and the hairpin ribozyme originally derived from the negative strand of the tobacco ringspot virus satellite RNA (sTRSV) (Sullivan 1994, U.S. Pat. No. 5,225,347[39]). Hammerhead and hairpin ribozyme motifs are most commonly adapted for trans cleavage of mRNAs for gene therapy (Sullivan 1994). Hairpin ribozymes are preferably used in the present invention. In general, the ribozyme is from 30 to 100 nucleotides in length.

Pharmaceutical Formulations

When employed as pharmaceuticals, the antisense oligonucleotides are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound. The pharmaceutical composition is, for example, administered intravenously. It is contemplated that the pharmaceutical composition may be administered directly into the tumor to be treated.

This invention also includes pharmaceutical compositions which contain, as the active ingredient, one or more of the antisense oligonucleotides associated with pharmaceutically acceptable carriers or excipients. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 3 mg to about 3 g, more usually about 10 mg to about. 1.5 g, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The antisense oligonucleotide is effective over a wide dosage range and is generally administered in a pharmaceutically effective amount. An effective amount is that amount which when administered alleviates the symptoms. Preferably the effective amount is that amount able to inhibit tumor cell growth. Preferably the effective amount is from about 0.1 mg/kg body weight to about 20 mg/kg body weight. It will be understood, however, that the amount of the antisense oligonucleotide actually administered will be determined by a physician, in the light of the relevant circumstances, including the condition to be treated, the chosen route of administration, the actual compound administered, the age, weight, and response of the individual patient, the severity of the patient's symptoms, and the like. The course of therapy may last from several days to several months or until diminution of the disease is achieved.

For preparing solid compositions such as tablets, the principal active ingredient/antisense oligonucleotide is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described herein. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

Another preferred formulation employed in the methods of the present invention employs transdermal delivery devices ("patches"). Such transdermal patches may be used to provide continuous or discontinuous infusion of the antisense oligonucleotides of the present invention in controlled amounts. The construction and use of transdermal patches for the delivery of pharmaceutical agents is well known in the art. See, for example, U.S. Pat. No. 5,023,252[40], herein incorporated by reference. Such patches may be constructed for continuous, pulsatile, or on demand delivery of pharmaceutical agents.

Another preferred method of delivery involves "shotgun" delivery of the naked antisense oligonucleotides across the dermal layer. The delivery of "naked" antisense oligonucleotides is well known in the art. See, for example, Felgner et al., U.S. Pat. No. 5,580,859[41]. It is contemplated that the antisense oligonucleotides may be packaged in a lipid vesicle before "shotgun" delivery of the antisense oligonucleotide.

The following formulation examples illustrate representative pharmaceutical compositions of the present invention.

Formulation Example 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, starch, and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 mL dose are made as follows:

| Ingredient | Amount |
|---|---|
| Active Ingredient | 50 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

Formulation Example 9

A formulation may be prepared as follows:

| Ingredient | Quantity |
|---|---|
| Active Ingredient | 5.0 mg |
| Corn Oil | 1.0 mL |

Formulation Example 10

A topical formulation may be prepared as follows:

| Ingredient | Quantity |
|---|---|
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Other suitable formulations for use in the present invention can be found in *Remington's Pharmaceutical Sciences*[23].

The antisense oligonucleotides or the pharmaceutical composition comprising the antisense oligonucleotides may be packaged into convenient kits providing the necessary materials packaged into suitable containers.

The oligonucleotides and ribozymes of the invention modulate tumor cell growth. Therefore methods are provided for interfering or inhibiting tumor cell growth in a mammal comprising contacting the tumor or tumor cells with an antisense oligonucleotide of the present invention.

The term "contact" refers to the addition of an oligonucleotide, ribozyme, etc. to a cell suspension or tissue sample or to administering the oligonucleotides etc. directly or indirectly to cells or tissues within an animal.

The methods may be used to treat proliferative disorders including various forms of cancer such a leukemias, lymphomas (Hodgkins and non-Hodgkins), sarcomas, melanomas, adenomas, carcinomas of solid tissue, hypoxic tumors, squamous cell carcinomas of the mouth, throat, larynx and lung, genitourinary cancers such as cervical and bladder cancer, hematopoietic cancers, colon cancer, breast cancer, pancreatic cancer, renal cancer, brain cancer, skin cancer, liver cancer, head and neck cancers, and nervous system cancers, as well as benign lesions such as papillomas. Other proliferative disorders such as psoriasis and those involving arthrosclerosis, angiogenesis and viral infections are also included.

The oligonucleotides of the invention may also be used to treat drug resistant tumors. Examples of drug resistant tumors are tumors resistant to such chemotherapeutic agents as 5-fluorouracil, mitomycin C, methotrexate or hydroxyurea and tumors expressing high levels of P-glycoprotein which is known to confer resistance to multiple anticancer drugs such as colchicine, vinblastine and doxorubicin; or tumors expressing multi-drug resistance protein as described by Dreeley et al.[43]. Accordingly, it is contemplated that the oligonucleotides of the present invention may be administered in conjunction with or in addition to known anticancer compounds or chemotherapeutic agents. Chemotherapeutic agents are compound which may inhibit the growth of tumors. Such agents, include, but are not limited to, 5-fluorouracil, mitomycin C, methotrexate and hydroxyurea. It is contemplated that the amount of chemotherapeutic agent may be either an effective amount, i.e. an amount sufficient to inhibit tumor growth or a less than effective amount.

The oligonucleotides of the present invention have been found to reduce the growth of tumors that are metastatic such as MDA-MB-231 breast adenocarcinoma, HT-29 colon adenocarcinoma, A549 lung carcinoma, and A2058 melanoma cancer cells. In an embodiment of the invention, a method is provided for reducing the growth of metastastic tumors in a mammal comprising administering an amount of an oligonucleotide complementary to the thioredoxin mRNA or the thioredoxin reductase mRNA, or an oligonucleotide shown in Tables 1 and 2.

The oligonucleotides may be delivered using viral or non-viral vectors. Sequences may be incorporated into cassettes or constructs such that an oligonucleotide of the invention is expressed in a cell. Preferably, the construct contains the proper transcriptional control region to allow the oligonucleotide to be transcribed in the cell.

Therefore, the invention provides vectors comprising a transcription control sequence operatively linked to a sequence which encodes an oligonucleotide of the invention. The present invention further provides host cells, selected from suitable eucaryotic and procaryotic cells, which are transformed with these vectors.

Suitable vectors are known and preferably contain all of the expression elements necessary to achieve the desired transcription of the sequences. Phagemids are a specific example of such beneficial vectors because they can be used either as plasmids or as bacteriophage vectors. Examples of the vectors include viruses such as bacteriophages, baculoviruses, retroviruses, DNA viruses, liposomes and other recombination vectors. The vectors can also contain elements for use in either procaryotic or eucaryotic host systems. One of ordinary skill in the art will know which host systems are compatible with a particular vector.

The vectors can be introduced into the cells by stable or transient transfection, lipofection, electroporation and infection with recombinant viral vectors.

Additional features can be added to the vector to ensure its safety and/or enhance its therapeutic efficacy. Such features include, for example, markers that can be used to negatively select against cells infected with recombinant viruses. An example of such a negative selection marker is the TK gene which confers sensitivity to the antiviral gancyclovir. Features that limit expression to particular cell types can also be included. Such features include, for example, promoter and regulatory elements that are specific for the desired cell type.

Retroviral vectors are another example of vectors useful for the in vivo introduction of a desired nucleic acid because they offer advantages such as lateral infection and targeting specificity. Lateral infection is the process by which a single infected cell produces many progeny virions that infect neighboring cells. The result is that a large area becomes rapidly infected.

A vector to be used in the methods of the invention may be selected depending on the desired cell type to be targeted. For example, if breast cancer is to be treated, then a vector specific for epithelial cell may be used. Similarly, if cells of the hematopoietic system are to be treated, then a viral vector that is specific for blood cells is preferred.

Utility

The antisense oligonucleotides of the present invention may be used for a variety of purposes. They may be used to inhibit the expression of the thioredoxin gene in a mammalian cell, resulting in the inhibition of growth of that cell. They may be used to inhibit the expression of the thioredoxin reductase gene in a mammalian cell, resulting in the inhibition of growth of that cell. The oligonucleotides may be used as hybridization probes to detect the presence of the thioredoxin mRNA or the thioredoxin reductase mRNA in mammalian cells. When so used the oligonucleotides may be labeled with a suitable detectable group (such as a radioisotope, a ligand, another member of a specific binding pair, for example, biotin). Finally, the oligonucleotides may be used as molecular weight markers.

In order to further illustrate the present invention and advantages thereof, the following specific examples are given but are not meant to limit the scope of the claims in any way.

EXAMPLES

In the examples below, all temperatures are in degrees Celsius (unless otherwise indicated) and all percentages are weight percentages (also unless otherwise indicated).

In the examples below, the following abbreviations have the following meanings. If an abbreviation is not defined, it has its generally accepted meaning:

$\mu$M=micromolar mM=millimolar

M=molar
ml=milliliter
μl=microliter
mg=milligram
μg=microgram
PAGE=polyacrylamide gel electrophoresis
rpm=revolutions per minute
ΔG=free energy, a measurement of oligonucleotide duplex stability
kcal=kilocalories
FBS=fetal bovine serum
DTT=dithiothrietol
SDS=sodium dodecyl sulfate
PBS=phosphate buffered saline
PMSF=phenylmethylsulfonyl fluoride General Methods in Molecular Biology:

Standard molecular biology techniques known in the art and not specifically described were generally followed as in Sambrook et al.[24]; Ausubel et al.[25]; and Perbal[26].

Oligonucleotides

The antisense oligonucleotides were selected from the sequence complementary to the thioredoxin mRNA or the thioredoxin reductase mRNA such that the sequence exhibits the least likelihood of showing duplex formation, hairpin formation, and homooligomers/sequence repeats but has a high potential to bind to the thioredoxin mRNA sequence or the thioredoxin reductase mRNA sequence, respectively. In addition, a false priming to other frequently occurring or repetitive sequences in human and mouse was eliminated. These properties were determined using the computer modeling program OLIGO® Primer Analysis Software, Version 5.0 International Biosciences, Inc. Plymouth, Minn.). With regard to the antisense oligonucleotides directed to thioredoxin, 5 oligonucleotides (2601–2605) were selected to target the 5' untranslated region, 2 oligonucleotides (2606–2607) targeted around the translation initiation site, 12 oligonucleotides (2608–2619) targeted the coding region, while 7 oligonucleotides (2620–2626) hybridized to the 3' untranslated region. A total of 66 different antisense oligonucleotides were designed and then ordered from either Dalton Chemical Laboratories, Inc. (North York, Canada) or TriLink Biotechnologies, Inc. (San Diego, Calif.)

Cell Lines

Human normal embryonic lung cell line WI-38 and ten different human cancer cell lines including fibrosarcoma (HT-1080), lung carcinoma (A549), ovary adenocarcinoma (SK-OV-3), hepatocellular carcinoma (Hep G2), melanoma (C8161), breast adenocarcinoma (MDA-MB-231), metastatic pancreatic adenocarcinoma (AsPC-1), colon adenocarcinoma (HT-29), cervical carcinoma (HeLa S3), human melanoma cell line A2058, human pancreatic cancer SU.86.86 were obtained from American Type Culture Collection (ATCC). The cell lines were maintained in α-MEM medium (Gibco BRL, Gaithersburg, Md.) supplemented with 10% fetal bovine serum (FBS).

Example 1

Overexpression of Thioredoxin in Human Cancer Cell Lines

Aliquots of cell suspension from different cell lines were added to tissue culture dishes and grown to subconfluency (70–80%). The level of thioredoxin mRNA or protein was determined by Northern or Western blot analysis, respectively.

Northern blot analysis was performed as previously described (Hurta and Wright[23]) with minor modifications. Briefly, total cellular RNA was prepared from cells using TRIzol reagent (Gibco BRL, Gaithersburg, Md.) at indicated times. mRNA (10–20 μg) was fractionated on 1.5% formaldehyde gels and transferred to nylon membranes. The blots were hybridized with $^{32}$P-labeled 300 bp PCR fragments synthesized using forward primer [SEQ ID NO:69] (5'-CAG ATC GAG AGC AAG ACT G-3'), reverse primer [SEQ ID NO:70] (5'-TTC ATT AAT GGT GGC TTC AA-3') and human liver 5'-stretch plus cDNA library (Clontech, Palo Alto, Calif.) as the template. The thioredoxin nucleotide sequence information was obtained from Genbank accession number X77585. Human thioredoxin mRNA was expressed as a 520 bp transcript (Tagaya et al.[28]) and was visualized and quantified using autoradiography or phosphorimager (Molecular Dynamics, Sunnyvale, Calif.).

Glyceraldehyde-3-phosphate dehydrogenase (GAPDH) mRNA was simultaneously probed for RNA loading controls. Again PCR was used to generate a 308 bp GAPDH DNA probe using forward primer [SEQ ID NO:71] (5'-CGC GGG GCT CTC CAG AAC AT-3') and reverse primer [SEQ ID NO:72] (5'-GCA ATG CCA GCC CCA GCG TC-3') from the same cDNA library as described above.

As clearly indicated in FIG. 1A, thioredoxin mRNA showed significantly higher levels of expression compared to normal cells in all nine different tumor cell lines. The degree of expression, however, varied among different cell lines and exhibited approximately 1.5 to 5.6 fold ranges of over-expression.

Whole cell protein extracts were prepared in 50–150 μl of 2× sample loading buffer (100 mM Tris-HCl, pH 6.8, 0.2M DTT, 4% SDS, 20% glycerol, and 0.015% bromophenol blue). Western blot analysis was performed as previously described (Choy et al.[29] and Fan et al.[30]) with some modifications. The protein extracts (10–20 μg) were fractionated on a 15% SDS-PAGE gel, transferred to nitrocellulose membranes and visualized by India ink staining. The expression of the thioredoxin was detected with anti-thioredoxin antibody (0.2–1 μg/ml) (American Diagnostica Inc., Greenwich, Conn.) followed by horseradish peroxidase-conjugated antigoat IgG (Sigma, St. Louis, Mo.) at a dilution of 1:8,000. A protein of approximately 12 kDa was visualized by ECL (Amersham, Arlington Heights, Ill.).

As shown in FIG. 1B, there was a significant correlation between the levels of thioredoxin mRNA and protein, as the protein expression pattern closely followed the extent of variations observed in the mRNA expression pattern. The lower panel of FIG. 1B shows that the total protein loading was consistent across the panel.

Example 2

The Inhibition of Growth of Cancer Cell Lines by Antisense Oligonucleotides Complementary to Thioredoxin The colony forming ability of cancer cell lines treated with 26 different antisense oligonucleotides was estimated using a method previously described (Choy et al.[29]). Specifically, aliquots of a tumor cell suspension were seeded into tissue culture dishes at a density of approximately $1\times10^4$ and incubated overnight at 37° C. in α-MEM medium supplemented with 10% FBS. Cells were washed once in 5 ml of PBS and treated with 0.2 μM of the indicated antisense oligonucleotide in the presence of cationic lipid (Lipofectin reagent, final concentration, 5 μg/ml, Gibco-BRL, Gaithersburg, Md.) for 4 hours. The antisense oligonucleotides were removed by washing the cells once with PBS and the cells were cultured in growth medium (α-MEM medium supplemented with 10% FBS) for 7 to 10 days at 37° C. Colonies were stained with methylene blue and scored by direct counting as described (Choy et al.[29] and Huang and Wright[31]). Percent inhibition was calculated by comparison with the number of colonies present in cultures grown in the absence of antisense oligonucleotides. All experiments were performed in quadruplicate.

Figure 3B:
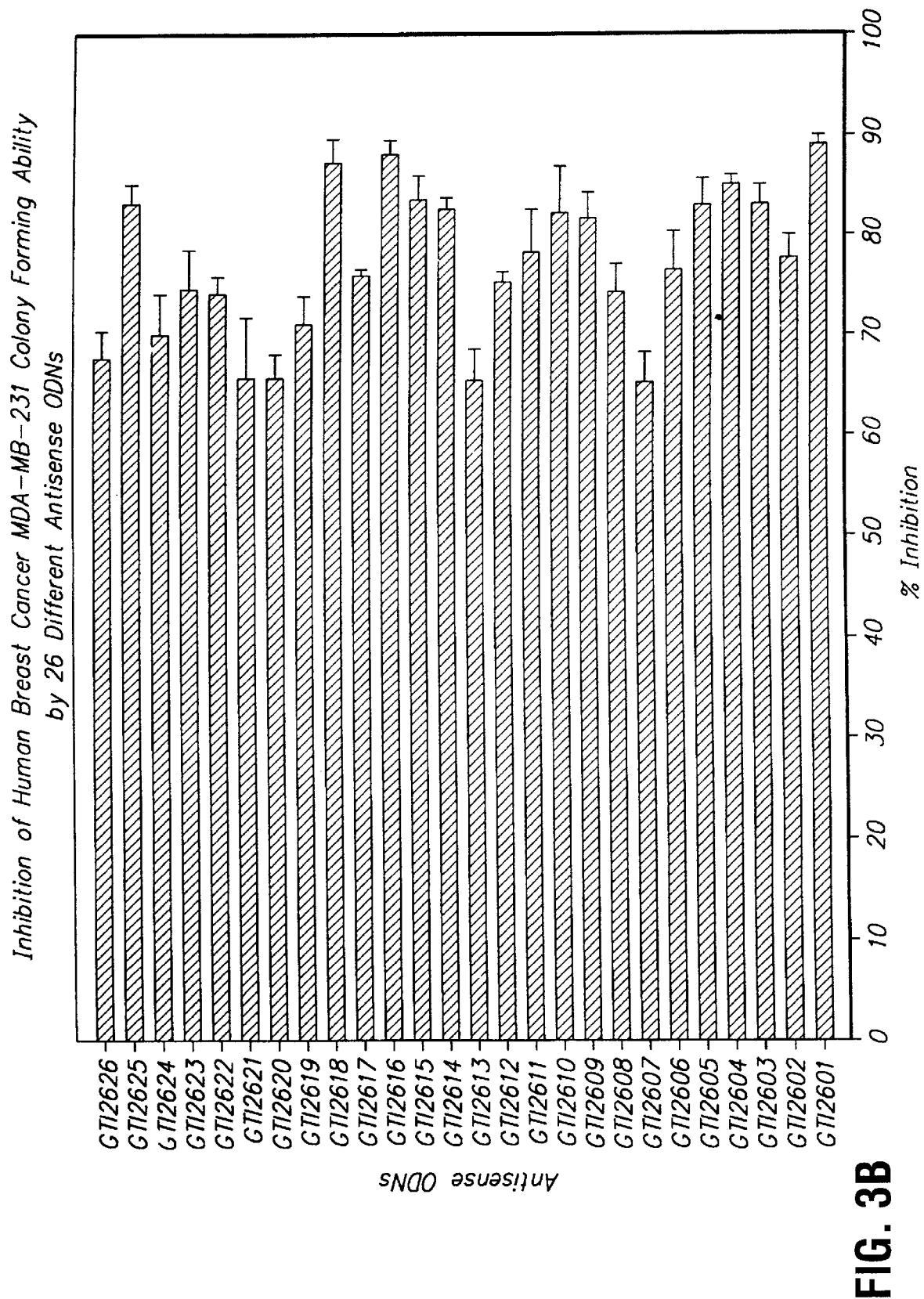
Figure 3C:
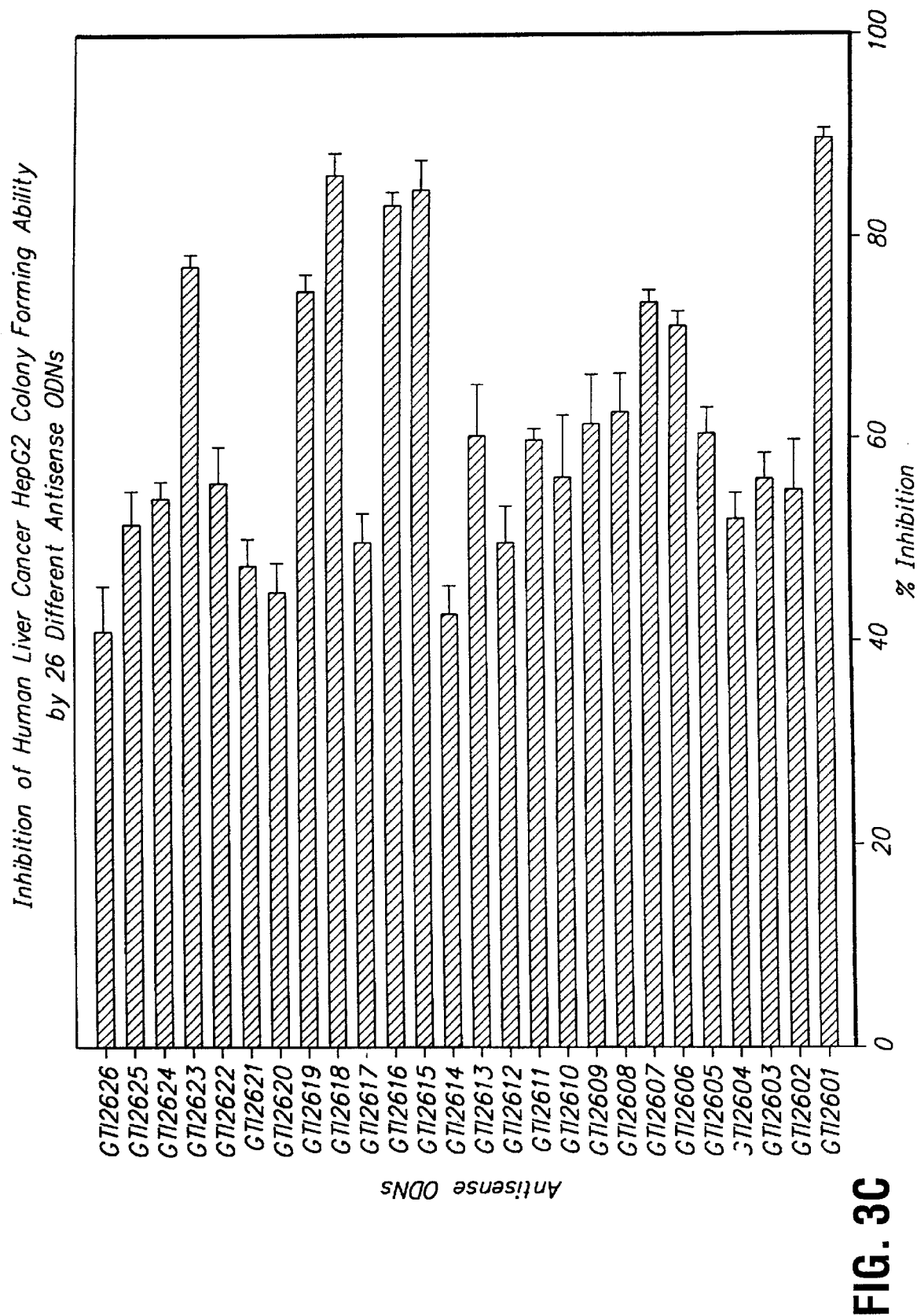
Figure 3D:
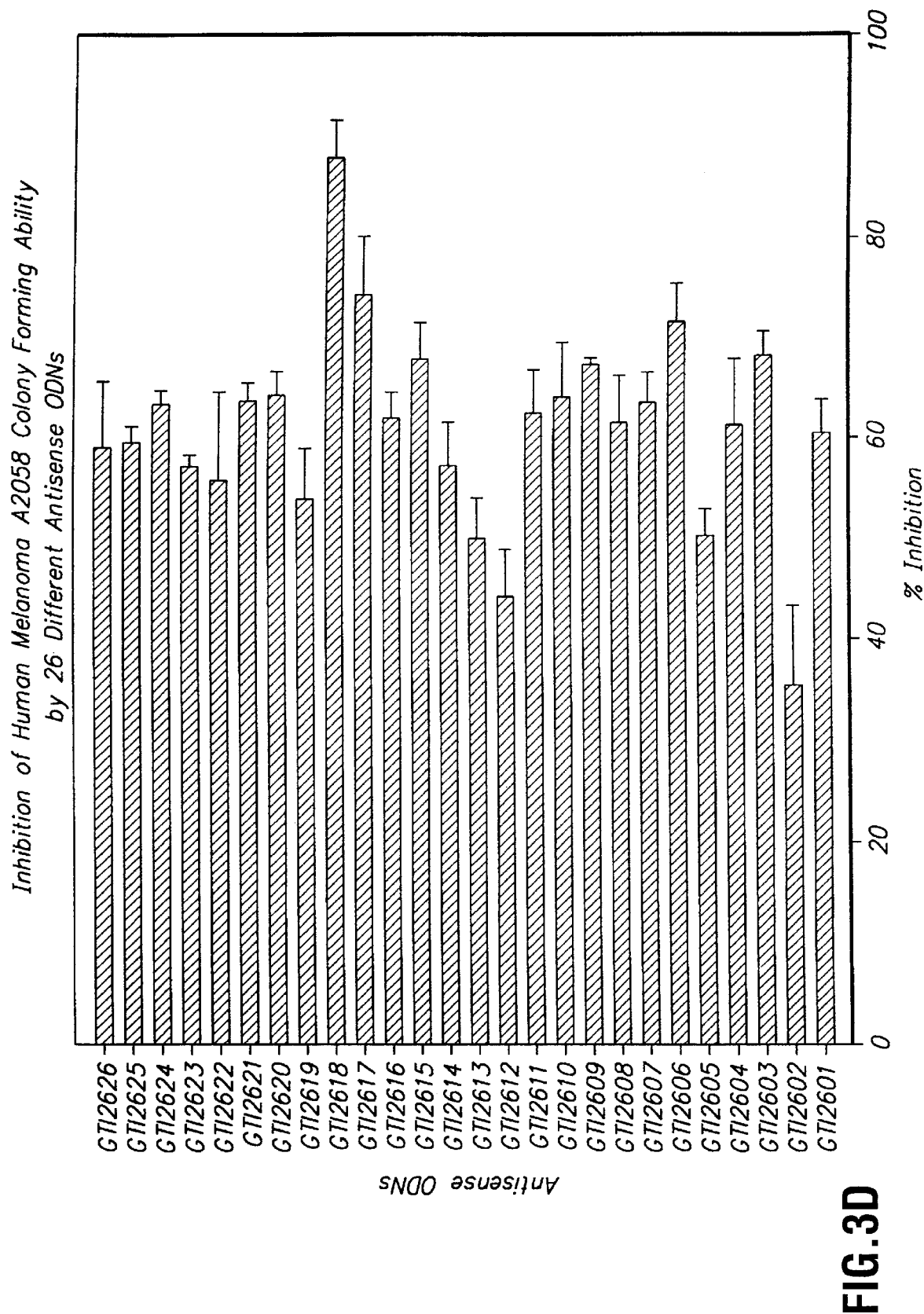
Figure 3E:
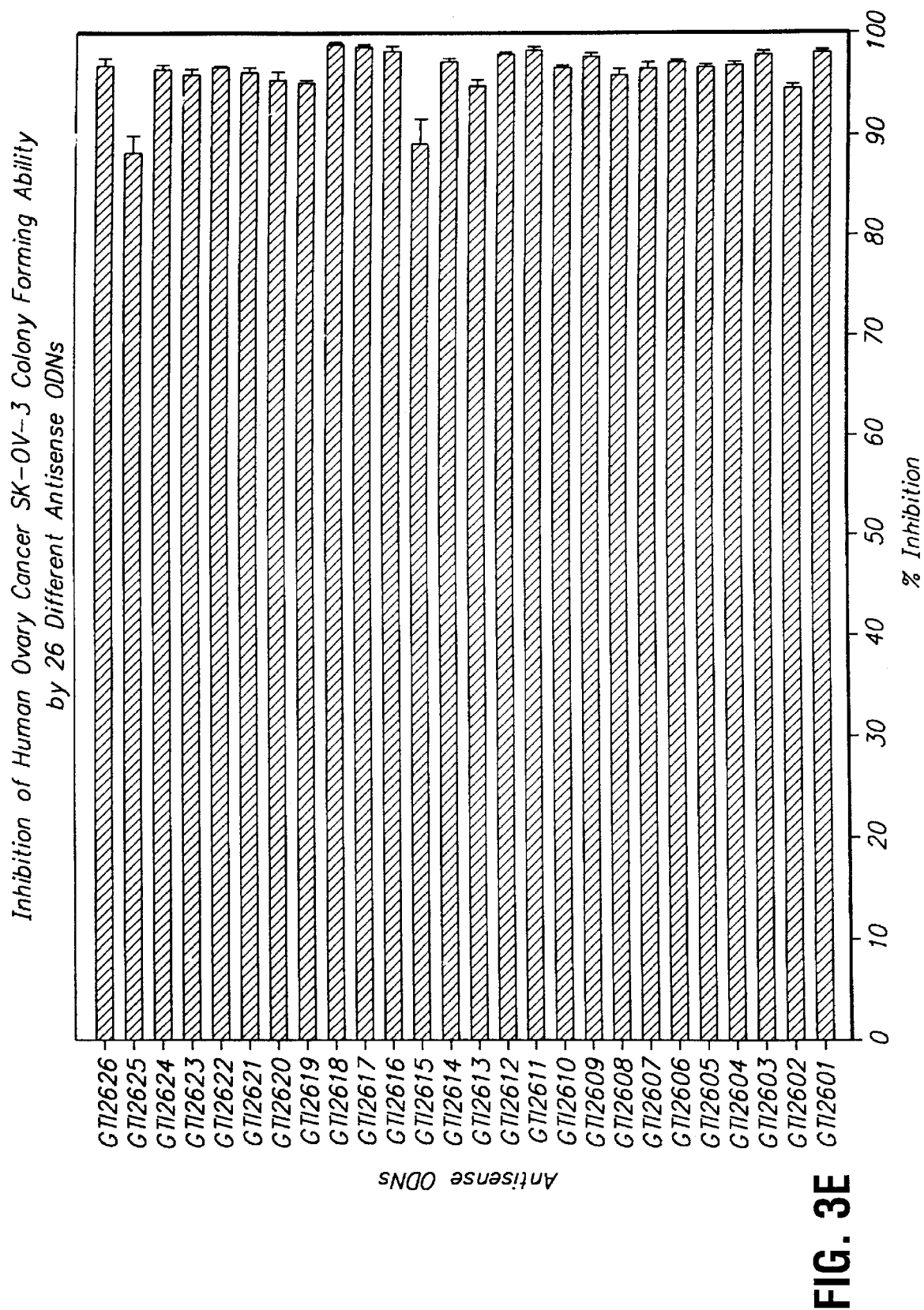
Figure 3F:
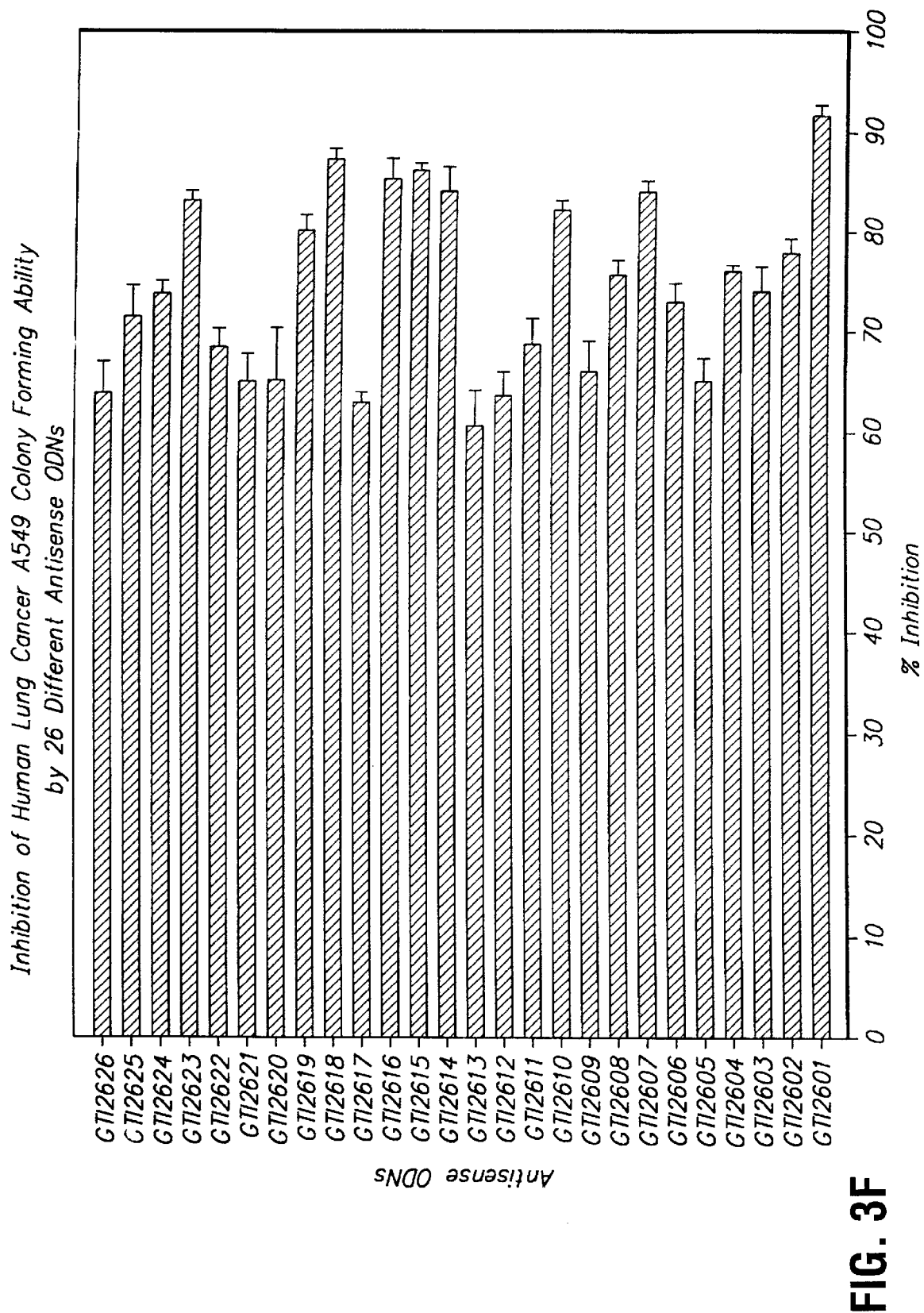

The antisense oligonucleotides exerted inhibitory effects on the colony forming ability of the human tumor cell lines. The percent inhibition of each antisense oligonucleotide is shown in FIG. 3A for human colon cancer cell line HT-29; FIG. 3B for human breast cancer cell line MDA-MB-231; FIG. 3C for human liver cancer cell line HepG2: FIG. 3D for human melanoma cell line A2058; FIG. 3E for human ovary cancer cell line SK-OV-3; and FIG. 3F for human lung cancer cell line A549.

Example 3

Figure 4A:
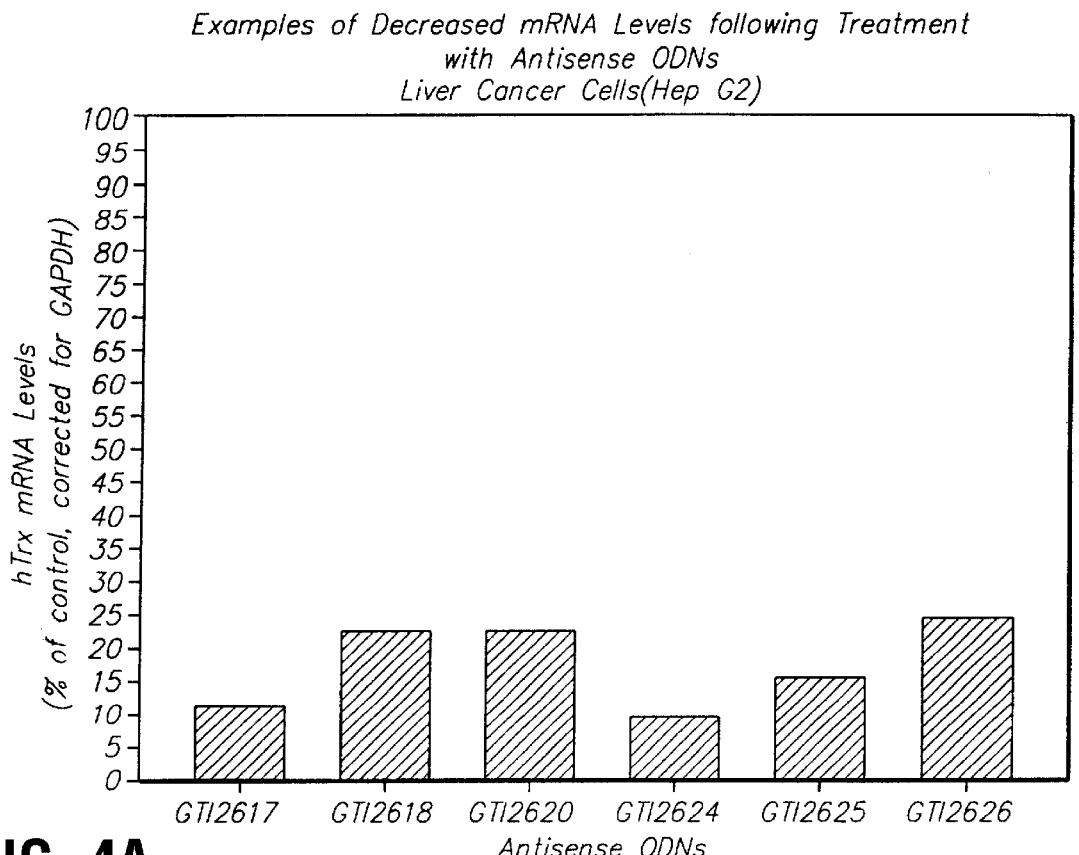
FIG. 4A is a graph showing the decreased thioredoxin mRNA levels in the human liver cancer cell line HepG2 following treatment with 6 antisense oligonucleotides complementary to the thioredoxin mRNA as a percentage of the mRNA levels in the untreated cell line.
Figure 4B:
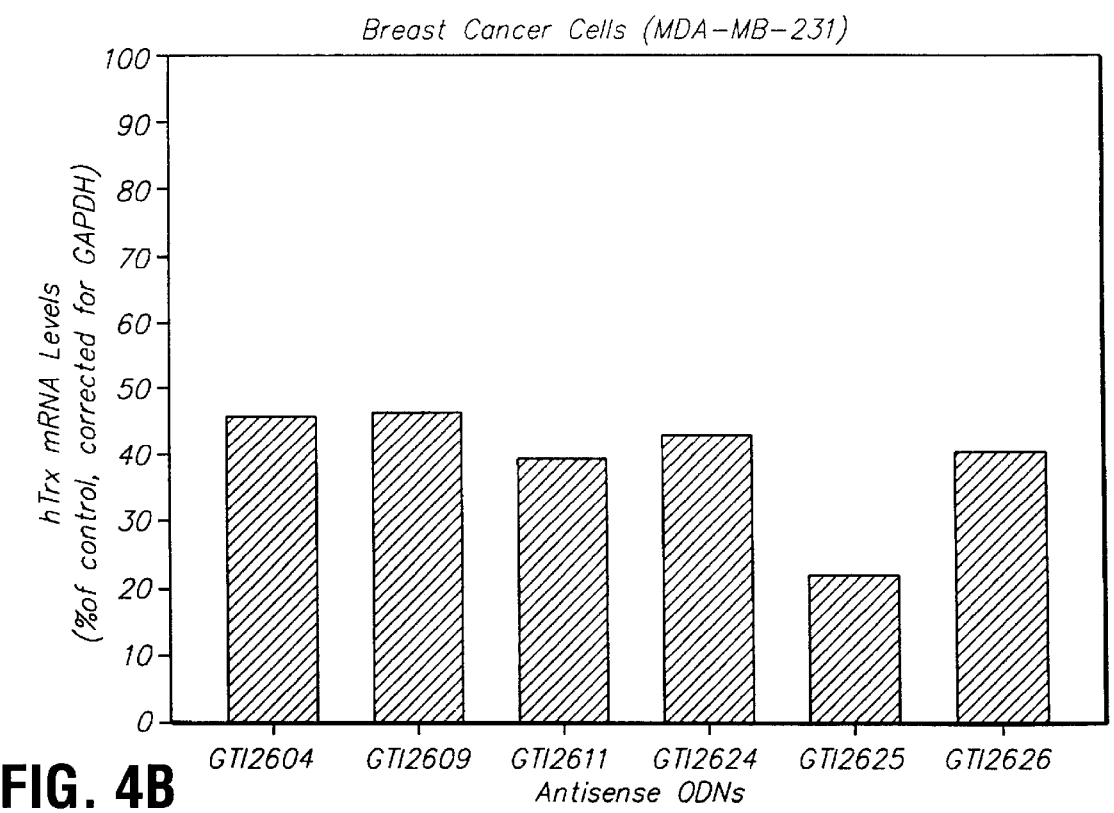
FIG. 4B is a graph showing the decreased thioredoxin mRNA levels in the human breast cancer cell line MDA-MB-231 following treatment with 6 antisense oligonucleotides complementary to the thioredoxin mRNA as a percentage of the mRNA levels in the untreated cell line.

Decreased mRNA Levels Following Treatment with Antisense Oligonucleotides Complementary to Thioredoxin Human liver cancer cells (Hep G2) or breast cancer cells (MDA-MB-231) were grown to subconfluency (70–80%) and were treated with 0.2 μM of phosphorothioate antisense oligonucleotides complementary to thioredoxin for 4 hours in the presence of cationic lipid (Lipofectin reagent, final concentration, 5 μg/ml, Gibco-BRL) and Opti-MEM (Gibco-BRL). Cells were washed once with PBS and incubated for 16 hours in α-MEM medium (Gibco-BRL) containing 10% FBS. Total RNA was prepared in TRIzol reagent (Gibco-BRL) and Northern blot analysis was performed as described earlier. Human thioredoxin mRNA levels were quantitated and normalized to GAPDH mRNA levels and illustrated as a percentage of the thioredoxin mRNA level obtained from untreated cells. FIGS. 4A and 4B show that the antisense oligonucleotides reduce the thioredoxin mRNA levels to at least 50% of the control cells.

Example 4

Reduction in Thioredoxin Protein Expression in Various Cell Lines After Treatment with Antisense Oligonucleotides Complementary to Thioredoxin Various cell lines were grown to subconfluency (70–80%) and were treated with 0.2 μM of phosphorothioate antisense oligonucleotides for 4 hours in the presence of cationic lipid (Lipofectin reagent, final concentration, 5 μg/ml, Gibco-BRL) and Opti-MEM (Gibco-BRL). Cells were washed once with PBS and incubated for 20 hours in α-MEM medium (Gibco-BRL) containing 10% FBS. The treatments and incubations were then repeated once more before the whole cell protein extracts were prepared in 2× sample loading buffer (100 mM Tris-HCl, pH 6.8, 0.2M DTT, 4% SDS, 20% glycerol, and 0.015% bromophenol blue) and Western blot analysis was performed as previously described (Choy et al.[29] and Fan et al.,[30]) with some modifications. The expression of thioredoxin was detected with anti-thioredoxin antibody (0.2–1 μg/ml) (American Diagnostica Inc., Greenwich, Conn.) followed by horseradish peroxidase-conjugated antigoat IgG (Sigma, St. Louis, Mo.) at a dilution of 1:8,000. A protein of approximately 12 kDa was visualized by ECL (Amersham, Arlington Heights, Ill.).

Figure 5A:
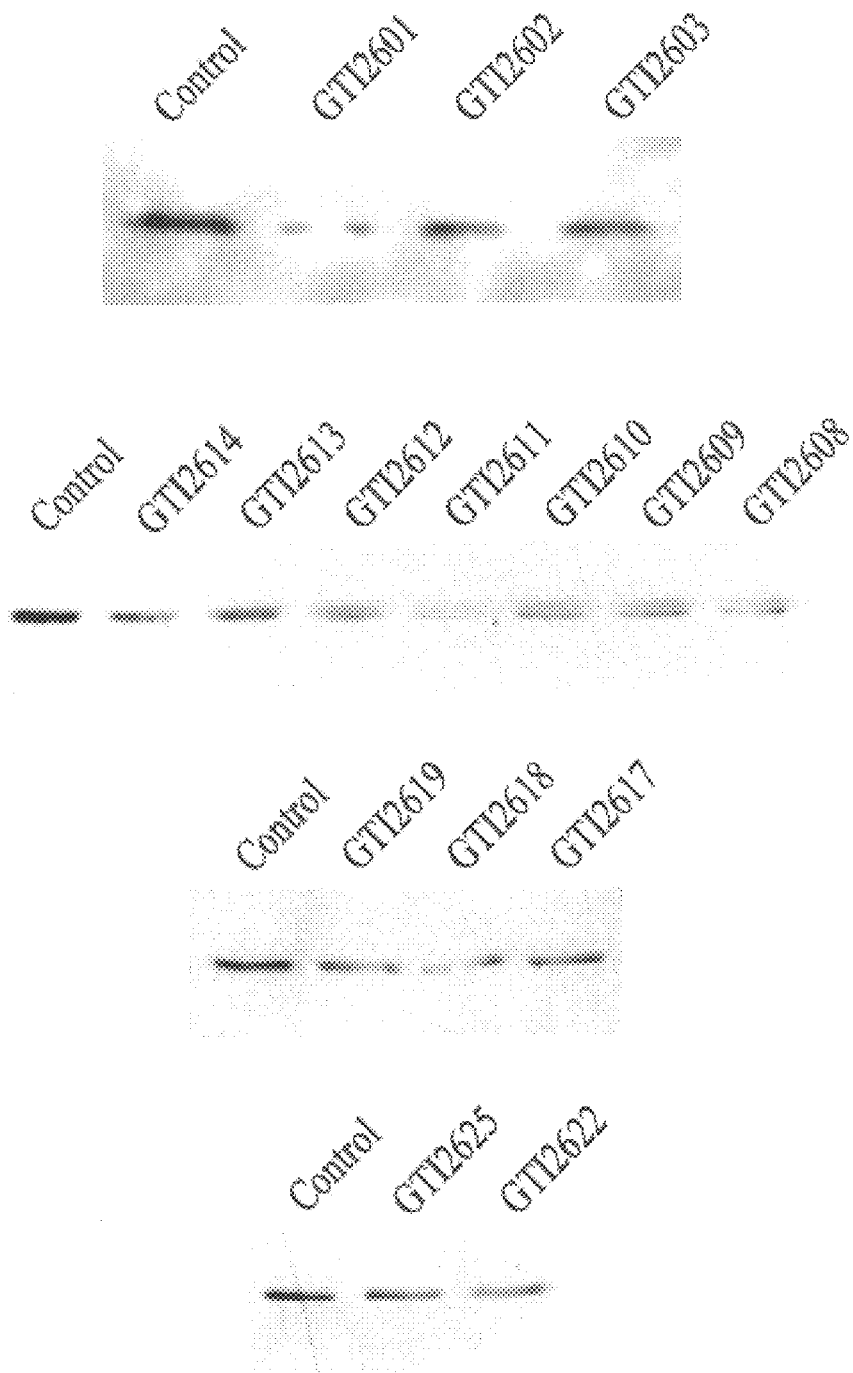
FIG. 5A is a photograph of a Western blot showing the level of thioredoxin protein expressed in the human colon cancer cell line HT-29 following treatment with the indicated antisense oligonucleotides.
Figure 5B:
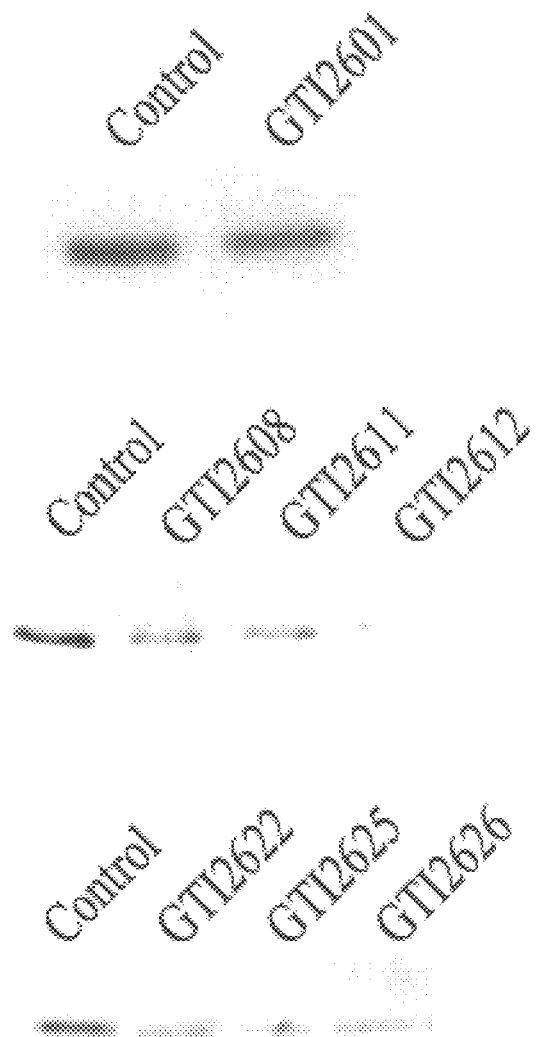
FIG. 5B is a photograph of a Western blot showing the level of thioredoxin protein expressed in the human breast cancer cell line MDA-MB-231 following treatment with the indicated antisense oligonucleotides.

The cell lines tested were human colon cancer cells HT-29 (FIG. 5A) and MDA-MB-231 human breast cancer cells (FIG. 5B). The level of protein was reduced by treatment with the indicated antisense oligonucleotides.

Figure 5C:
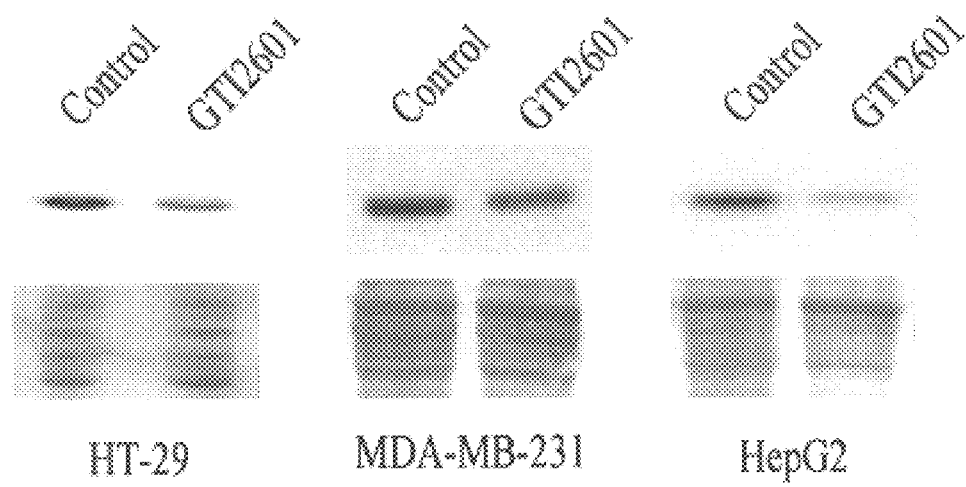
FIG. 5C is a photograph of a Western blot showing the level of thioredoxin protein expressed in the human colon cancer cell line HT-29, the human breast cancer cell line MDA-MB-231, and the human liver cancer cell line HepG2 following treatment with the antisense oligonucleotide 2601 [SEQ ID NO:1]. The lower panel shows that protein loading was consistent across the panel.

Three different human tumor cell lines (HT-29, MDA-MB-231 and HepG2 for colon, breast and liver cancer, respectively) were treated with 0.2 μM of oligonucleotide 2601 [SEQ ID NO: 1] as indicated above. FIG. 5C shows the inhibition of thioredoxin protein expression by the antisense oligonucleotide in each of the cell lines. The lower panel shows that the protein loading was consistent across the panel.

Example 5

Inhibition of Human Tumor Cell Growth in Mice by Intravenous Treatment with Antisense Oligonucleotides Complementary to Thioredoxin CD-1 athymic nude mice were purchased from Charles River Laboratories (Montreal Canada). HT-29 human colon cancer cells (typically $3 \times 10^6$ cells in 100 μl of PBS) were subcutaneously injected into the right flank of 6–7 weeks old CD-1 athymic female nude mice. Each experimental group included 5 mice. After the size of tumor reached an approximate volume of 100 mm$^3$, typically 5 days post tumor cell injection, different antisense oligonucleotides were administered by bolus infusion into the tail vein every other day at 10 mg/kg. Control animals received saline alone for the same period. Treatments typically lasted 10 days thereafter.

Figure 6A:
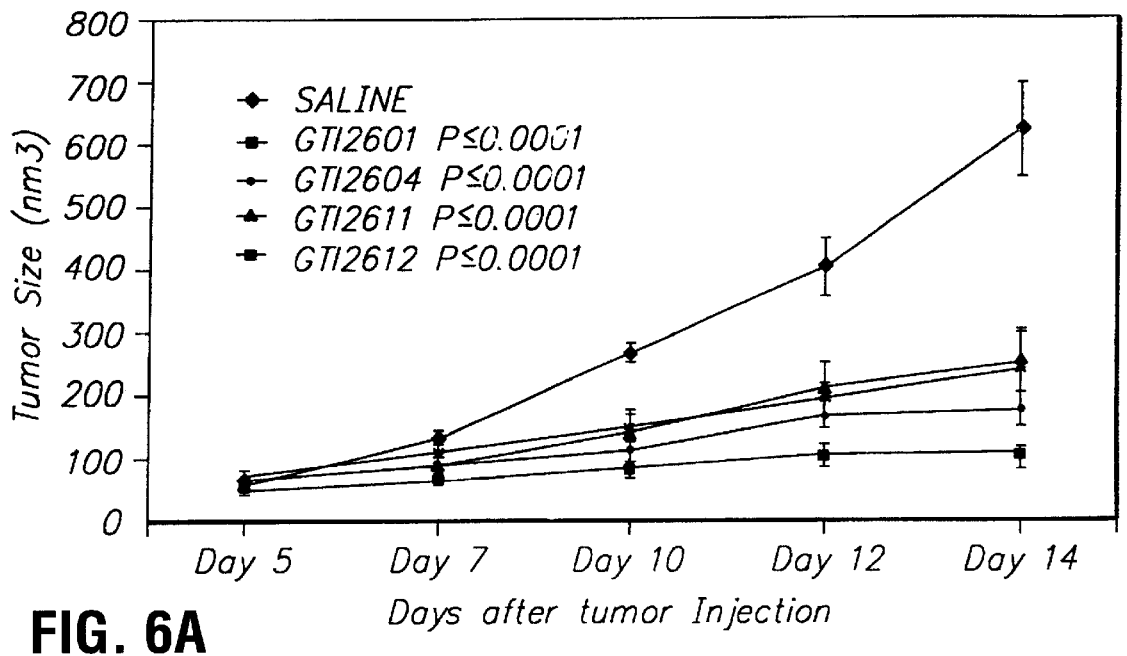
FIG. 6A is a chart of the size of a tumor in nude mice over time after intravenous treatment of the mice every second day with the indicated antisense oligonucleotides.

FIG. 6A shows the effects of the antisense oligonucleotides on HT-29 tumor growth in CD-1 nude mice. Antitumor activities were estimated by the inhibition of tumor volume, which was measured with a caliper on average of two day intervals over the span of 9 days. Each point in the figure represents mean tumor volume calculated from 5 animals per experimental group. Analysis of covariance was used to compare the regression curves of mice over time within each treatment group. specific hypothesis of equality of slopes, or equality of intercepts when slopes are equal are derived from the analysis. All analysis used the SAS (Statistical Analysis System) version 6.12. When compared to the saline control each antisense oligonucleotide shown in FIG. 6A inhibited the growth of the tumor with a p value of $\leq 0.0001$.

Figure 6B:
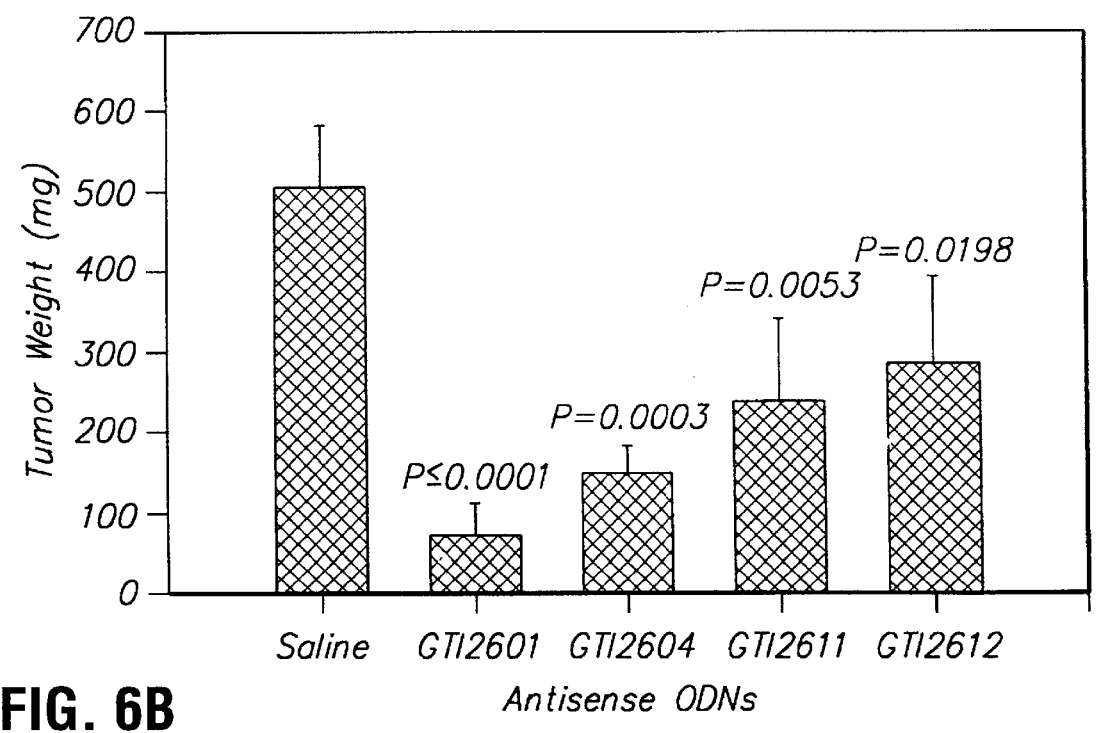
FIG. 6B is a graph of the weight of the tumor removed from the nude mice approximately 10 days after intravenous treatment of the mice every second day with the indicated antisense oligonucleotides.

At the end of the treatment (usually 24 hours after the last treatment) the animals were sacrificed and tumor weights were measured. FIG. 6B shows the mean weight of the tumors. The antisense oligonucleotides showed significant inhibitory effects on tumor growth. One-way analysis of variance was used to compare the means of groups of treatments. Where the overall group effect was significant, a priori multiple comparisons using the least square means was used to find the pairs of treatment groups that were significantly different. When tumor weight was compared each of the antisense oligonucleotides also showed statistically significant inhibition when compared to the saline control with p values of $\leq 0.0198$ (FIG. 6B).

Figure 6C:
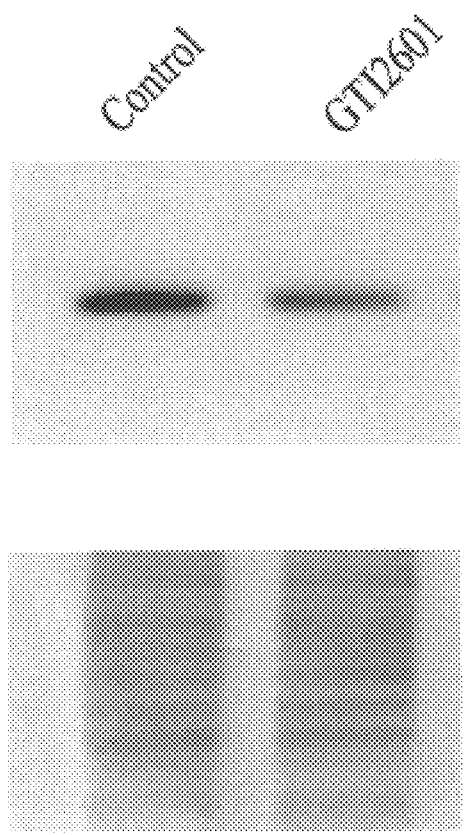
FIG. 6C is photograph of a Western blot showing the level of thioredoxin protein expression in the human colon cancer HT-29 tumors excised from the nude mice approximately 10 days after intravenous treatment of the mice every second day with the indicated antisense oligonucleotides. A part of the blot stained with India ink is shown below to demonstrate protein loading.

HT-29 human colon cancer cells were subcutaneously injected into the right flank of 6–7 weeks old CD-1 athymic female nude mice. After the size of tumor reached an approximate volume of 100 mm$^3$, typically 5 days post tumor cell injection, different antisense oligonucleotides were administered by bolus infusion into the tail vein every other day at 10 mg/kg. Control animals received saline alone for the same period. Mice were sacrificed after 8 injections and excised tumor fragments of similar size were immediately collected into RIPA extraction buffer (50 mM Tris-HCl, pH 7.5, 150 mM NaCl, 1% NP-40, 0.5% sodium deoxycholate, 0.1% SDS, 0.02% NaN$_3$, 1 mM PMSF and 10 µM leupeptin) and rapidly homogenized for protein preparation. To measure the effects of antisense oligonucleotides on thioredoxin protein levels, Western blot analysis was performed as previously described (Choy et al.[29] and Fan et al.[30]) with some modifications. The protein extracts (10–20 µg) were fractionated on a 12% SDS-PAGE gel, transferred to nitrocellulose membranes and visualized by India ink staining. The expression of thioredoxin was detected with anti-thioredoxin antibody (0.2–1 µg/ml) (American Diagnostica Inc., Greewich, Conn.) followed by horseradish peroxidase-conjugated antigoat IgG (Sigma, St. Louis, Mo.) at a dilution of 1:8,000. A protein of approximately 50 kDa was visualized by ECL (Amersham, Arlington Heights, Ill.). Protein loading in each lane was approximately the same; A part of the blot stained with India ink is shown underneath to demonstrate an equal loading in each lane. It is clear from FIG. 6C that the expression of thioredoxin is reduced in tumor tissue obtained from mice treated with antisense oligonucleotides targeting thioredoxin compared to control tumor tissue obtained from mice treated with saline.

Example 6

Overexpression of Thioredoxin Reductase in Human Tumor Cell Lines

Aliquots of cell suspension from different cell lines were added to tissue culture Petri dishes and grown to subconfluency (70–80%). The level of thioredoxin reductase mRNA was determined by Northern blot analysis.

Northern blot analysis was performed as previously described (Hurta and Wright[27]) with minor modifications. Briefly, total cellular RNA was prepared from cells using TRIzol reagent (Gibco-BRL, Gaithersburg, Md.) at indicated times. RNA (10–20 µg) was fractionated on 1.5% formaldehyde gels and transferred to nylon membranes. The blots were hybridized with $^{32}$P-labeled 330 bp PCR fragments synthesized using forward primer [SEQ ID NO:73] (5'-TTG GCT TAG AAA CCG TAG GG-3'), reverse primer [SEQ ID NO:74] (5'-CCA ATG GCC AAA AGT AAC TA-3') and human liver 5'-stretch plus cDNA library (Clontech, Palo Alto, Calif.) as the template. Human thioredoxin reductase mRNA was expressed as a 3826 nucleotide transcript (Gasdaska et al.[32]) and was visualized and quantified using autoradiography or phosphorimager (Molecular Dynamics, Sunnyvale Calif.).

Glyceraldehyde-3-phosphate dehydrogenase (GAPDH) mRNA was simultaneously probed for RNA loading controls. Again PCR was used to generate a 308 bp GAPDH DNA probe using forward primer [SEQ ID NO:71] (5'-CGC GGG GCT CTC CAG AAC AT-3') and reverse primer [SEQ ID NO:72] (5'-GCA ATG CCA GCC CCA GCG TC-3') from the same cDNA library as described above.

Figure 7:
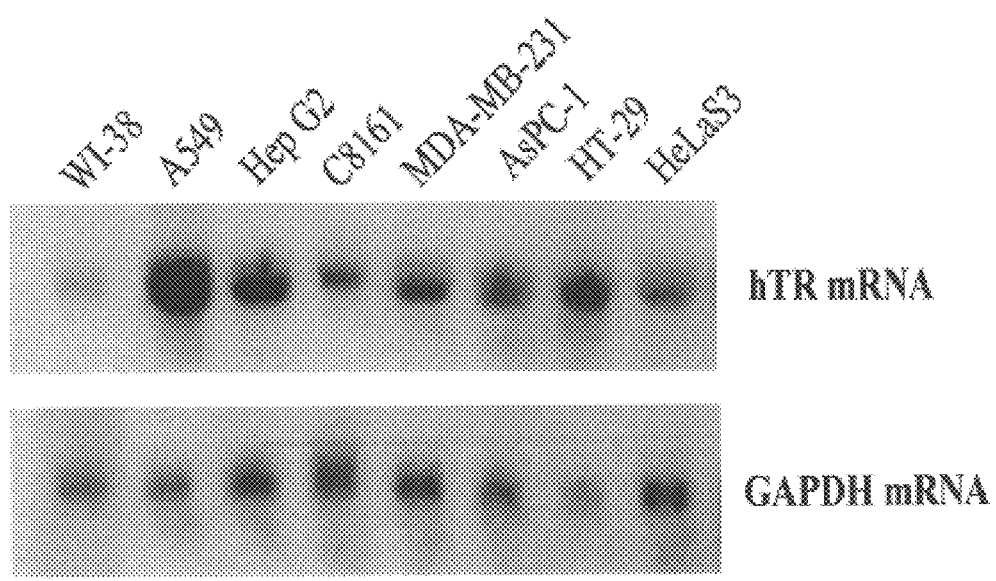
FIG. 7 is a autoradiograph of a Northern blot showing the level of thioredoxin reductase mRNA expressed in the indicated tumor cell lines.

As clearly indicated in FIG. 7, thioredoxin reductase mRNA in all nine different tumor cell lines showed significantly higher levels of expression compared to the normal cell line.

Example 7

The Inhibition of Growth of Cancer Cell Lines by Antisense Oligonucleotides Complementary to Thioredoxin Reductase The colony forming ability of cancer cell lines treated with 40 different antisense oligonucleotides was estimated using a method previously described (Choy et al.[29]). Specifically, aliquots of a tumor cell suspension were added to tissue culture dishes at a density of approximately 1×10$^4$ and incubated overnight at 37° C. in α-MEM medium supplemented with 10% FBS. Cells were washed once in 5 ml of PBS and treated with 0.2 µM of the indicated antisense oligonucleotide in the presence of cationic lipid (Lipofectin reagent, final concentration, 5 µg/ml, Gibco-BRL Gaithersburg, Md.) for 4 hours. The antisense oligonucleotides were removed by washing the cells once with PBS and the cells were cultured in growth medium (α-MEM medium supplemented with 10% FBS) for 7 to 10 days at 37° C. Colonies were stained with methylene blue and scored by direct counting as described (Choy et al.[29] and Huang and Wright[31]). Percent inhibition was calculated by comparison with number of colonies present in cultures grown in the absence of antisense oligonucleotides. All experiments were performed in quadruplicate.

Figure 8A:
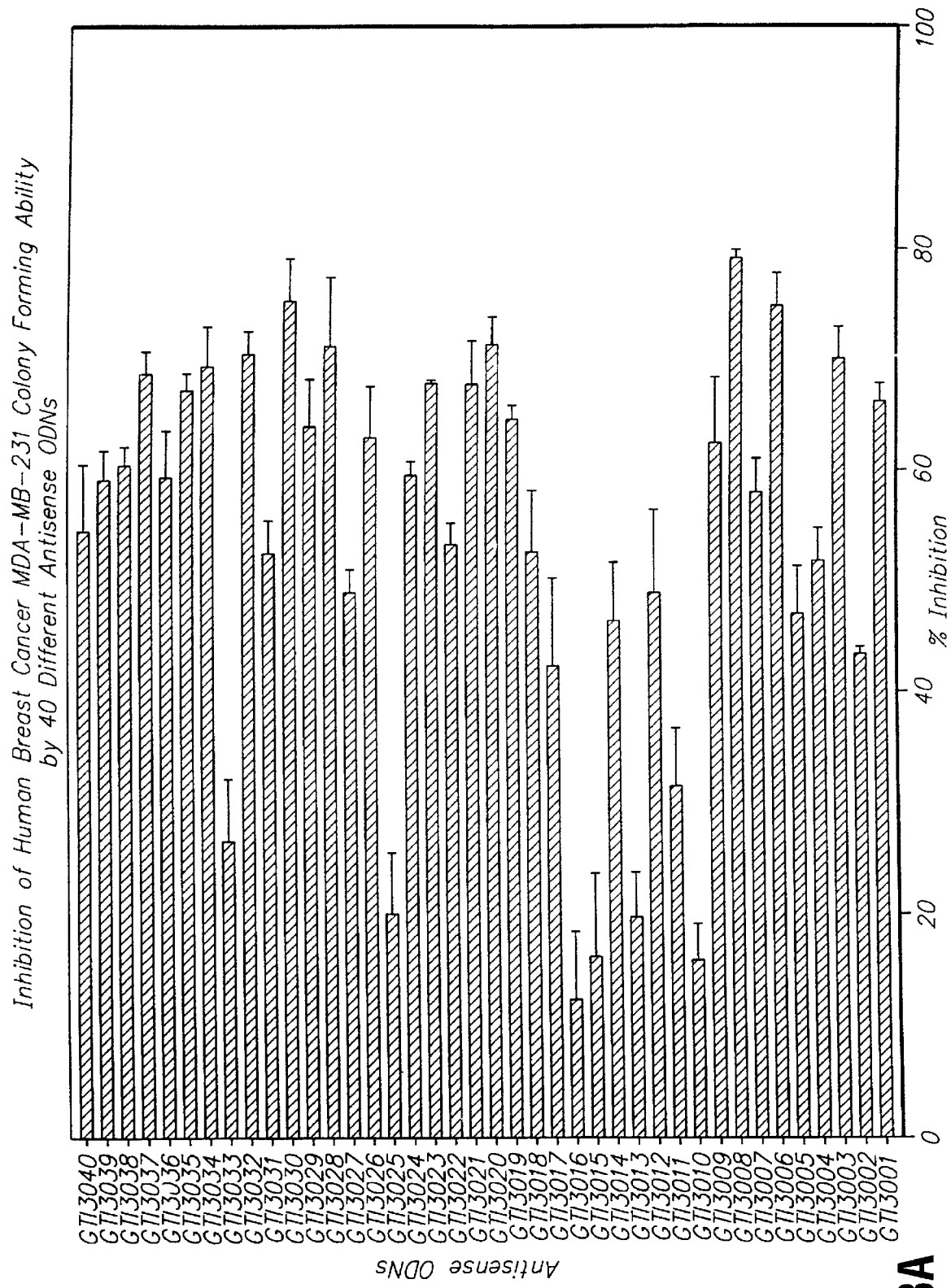
FIGS. 8A–8D are graphs showing the percentage of inhibition of various human cancer cell line's colony forming ability after treatment with 40 different antisense oligonucleotides complementary to the thioredoxin reductase mRNA. The cell lines tested were human breast cancer cell line MDA-MB-231 (FIG. 8A), human melanoma A2058 (FIG. 8B), human liver cancer HepG2 (FIG. 8C) and human pancreatic cancer SU.86.86 (FIG. 8D).
Figure 8B:
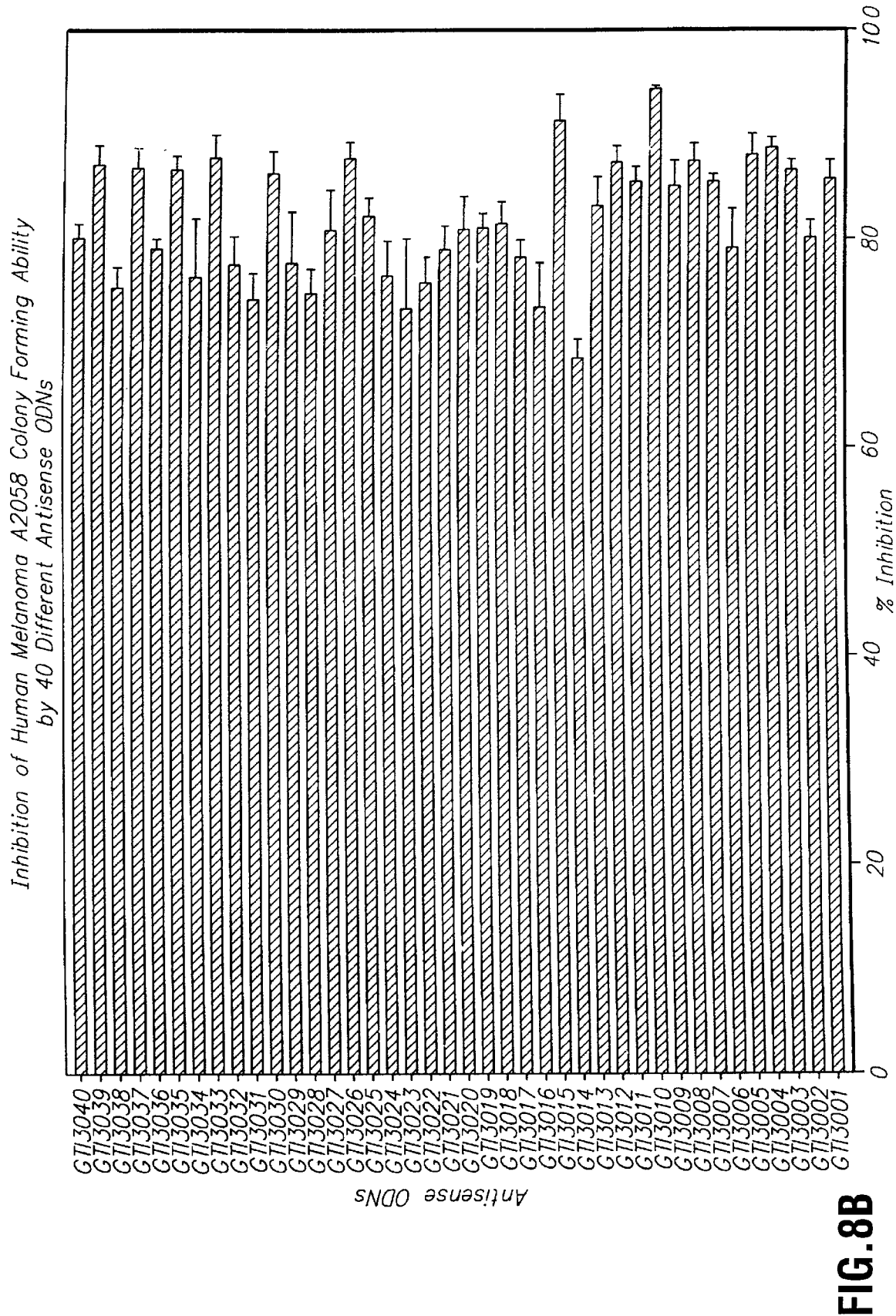
Figure 8C:
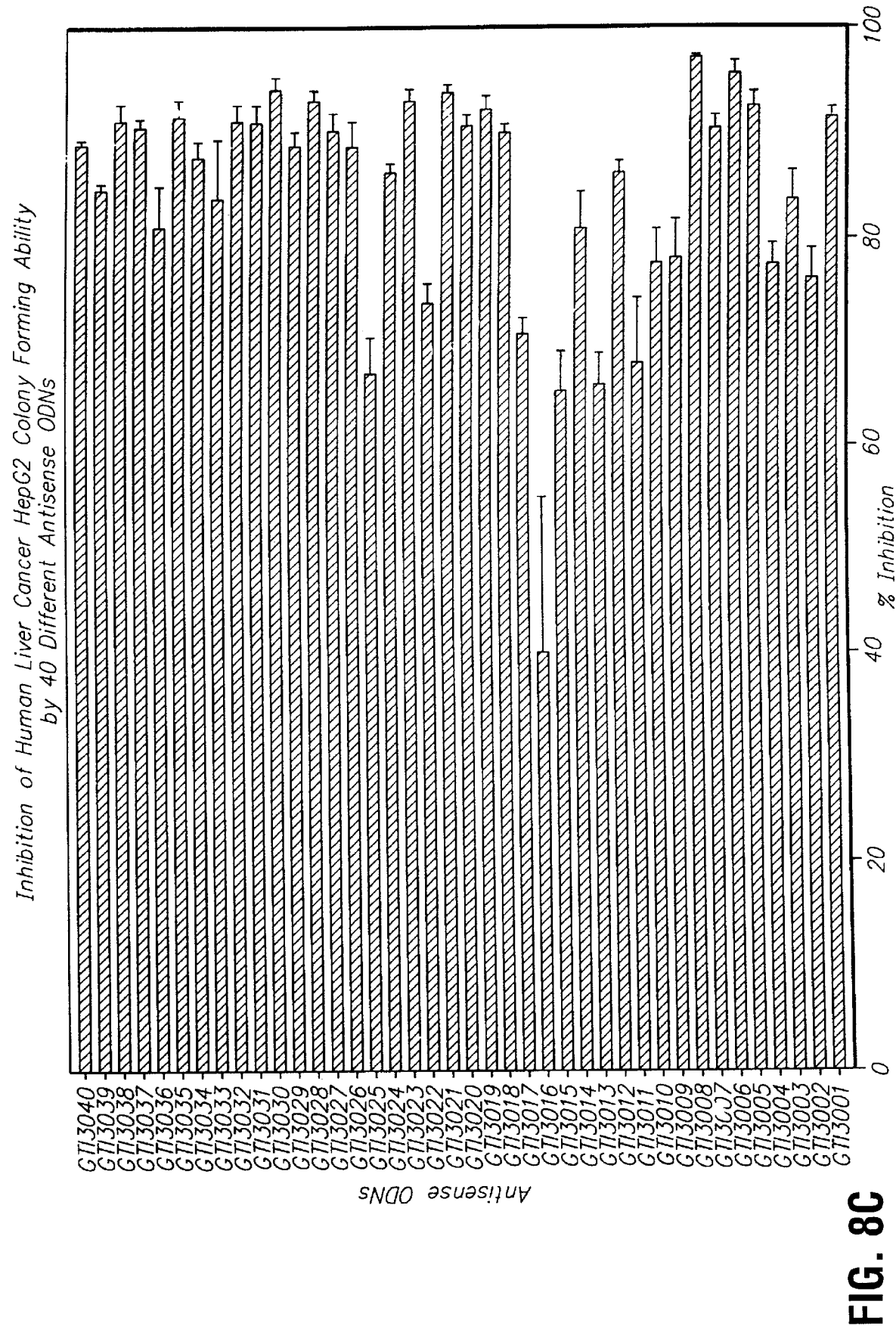
Figure 8D:
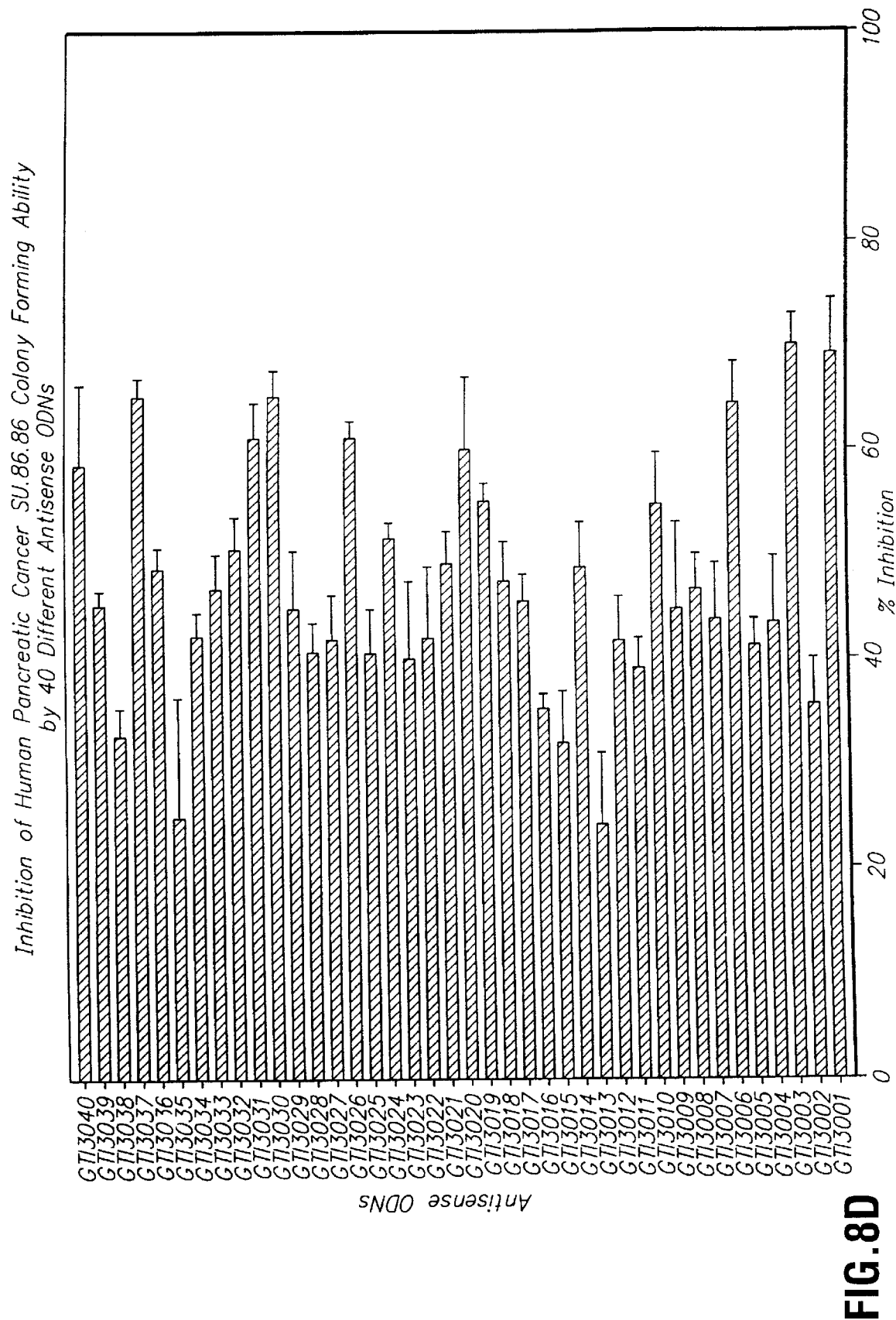

The majority of the antisense oligonucleotides exerted a moderate inhibitory effect on the colony forming ability of the human tumor cell lines. The percent inhibition of each antisense oligonucleotide is shown in FIG. 8A for human breast cancer cell line MDA-MB-231; FIG. 8B for human melanoma cell line A2058; FIG. 8C for human liver cancer cell line HepG2: and FIG. 8D for human pancreatic cancer cell line SU.86.86.

Example 8

Figure 9A:
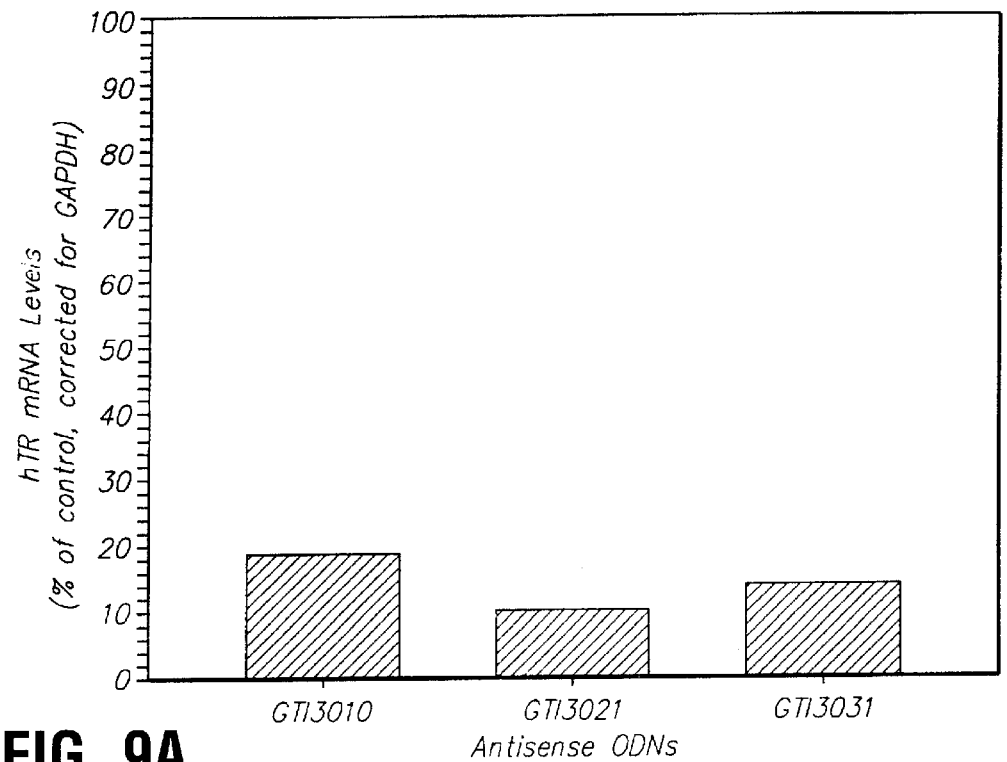
FIGS. 9A and 9B are graphs showing the level of expression of thioredoxin reductase mRNA in cell lines after treatment with the indicated antisense oligonucleotides as a percentage of the level of mRNA in the untreated cell line.
Figure 9B:
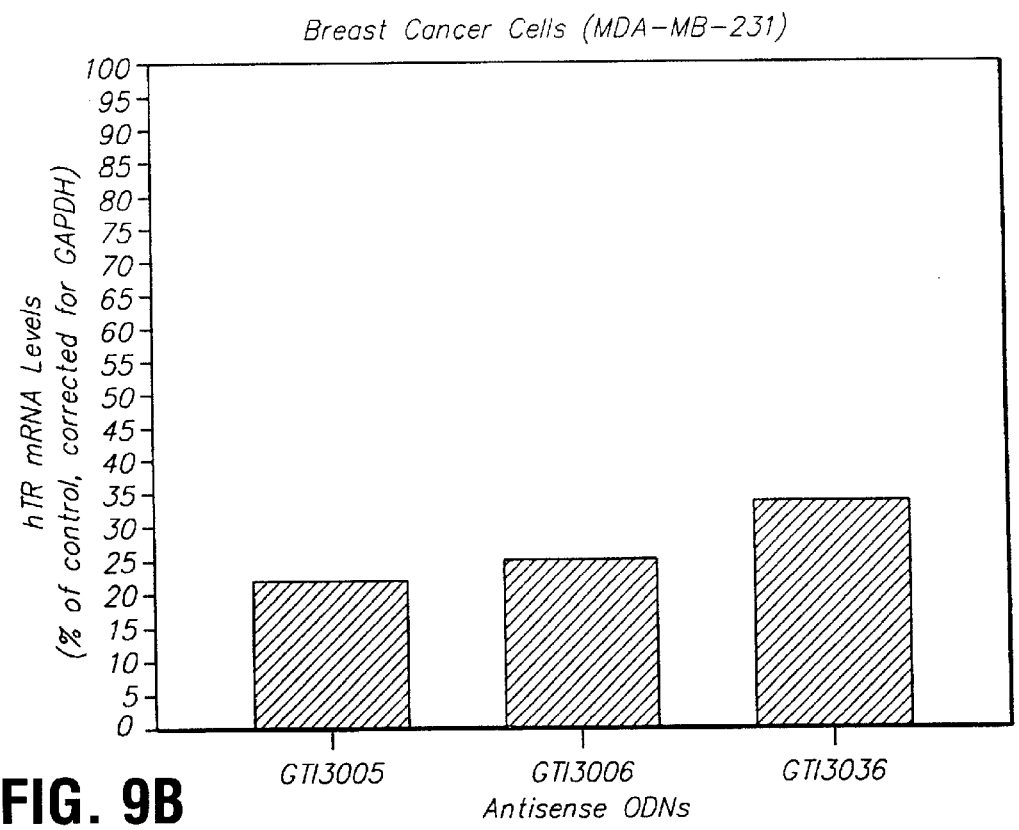

Decreased mRNA Levels Following Treatment with Antisense Oligonucleotides Complementary to Thioredoxin Reductase Human colon cancer cells (HT-29) or breast cancer cells (MDA-MB-231) were grown to subconfluency (70–80%) and were treated with 0.2 µM of phosphorothioate antisense oligonucleotides complementary to thioredoxin reductase for 4 hours in the presence of cationic lipid (Lipofectin reagent, final concentration, 5 µg/ml, GIBCO BRL) and Opti-MEM (Gibco-BRL). Cells were washed once with PBS and incubated for 16 hours in α-MEM medium (Gibco-BRL) containing 10% FBS. Total RNA was prepared in TRIzol reagent (Gibco-BRL) and Northern blot analysis was performed as described earlier. Human thioredoxin reductase mRNA levels were quantified and normalized to GAPDH mRNA levels and illustrated as a percentage of the thioredoxin reductase mRNA level obtained from untreated cells. FIGS. 9A and 9B show that the antisense oligonucleotides reduced the thioredoxin reductase mRNA levels to less than 50% of the control cell levels.

Example 9

Figure 10:
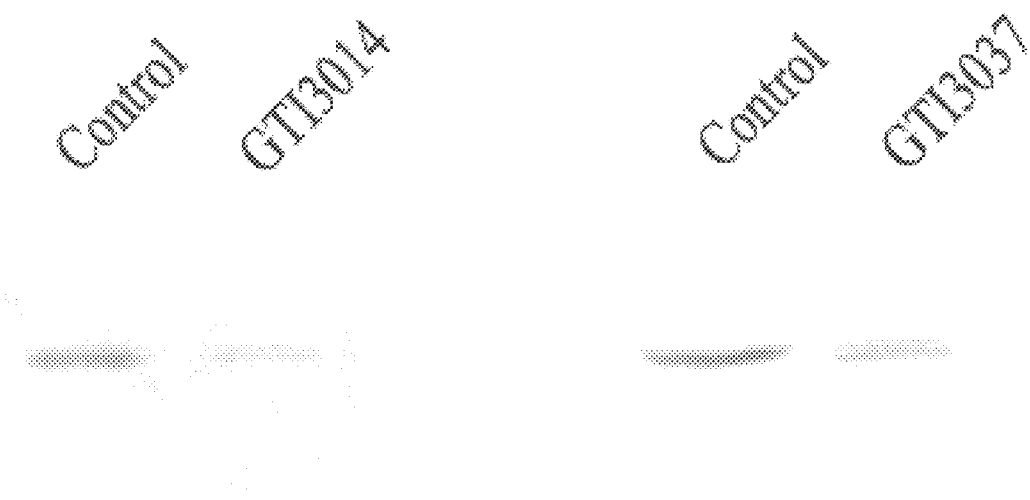
FIG. 10 is a photograph of a Western blot showing the level of thioredoxin reductase protein expression in human pancreatic cancer cell line AsPC-1 following treatment with antisense oligonucleotides 3014 and 3037 [SEQ ID NOs: 40 and 63].

Reduction in Thioredoxin Reductase Protein Expression in Cells after Treatment with Antisense Oligonucleotides AsPC-1 human pancreatic cancer cells were grown to subconfluency (70–80%) and were treated with 0.2 µM of phosphorothioate antisense oligonucleotides 3014 [SEQ ID NO:40] and 3037 [SEQ ID NO:63] for 4 hours in the presence of cationic lipid (Lipofectin reagent, final concentration, 5 µg/ml, GIBCO BRL) and Opti-MEM (Gibco-BRL). Cells were washed once with PBS and incubated for 20 hours in α-MEM medium (Gibco-BRL) containing 10% FBS. The treatments and incubations were then repeated once more before the whole cell protein extracts were prepared in 2× sample loading buffer (100 mM Tris- HCl, pH 6.8, 0.2M DTT, 4% SDS, 20% glycerol, and 0.015% bromophenol blue) and Western blot analysis was performed as previously described (Choy et al.[29] and Fan et al.[30]) with some modifications. The expression of the thioredoxin reductase was detected with anti-thioredoxin reductase antibody (0.2–1 µg/ml) (Research Genetics, Inc., Huntsville, Ala.) followed by horseradish peroxidase-conjugated antigoat IgG (Sigma, St. Louis, Mo.) at a dilution of 1:8,000. A protein of approximately 50 kDa was visualized by ECL (Amersham, Arlington Heights, Ill.). See FIG. 10.

Example 10

Inhibition of Tumor Cell Growth in Mice by Treatment with Antisense Oligonucleotides HT-29 human colon cancer cells (typically 3×10$^6$ cells in 100 µl of PBS) were subcutaneously injected into the right flank of 6–7 weeks old CD-1 athymic female nude mice. After the size of tumor reached an approximate volume of 100 mm$^3$, typically 5 days post tumor cell injection, different antisense oligonucleotides were administered by bolus infusion into the tail vein every other day at 10 mg/kg. Control animals received saline alone for the same period. Treatments typically lasted 10 days thereafter.

Figure 11A:
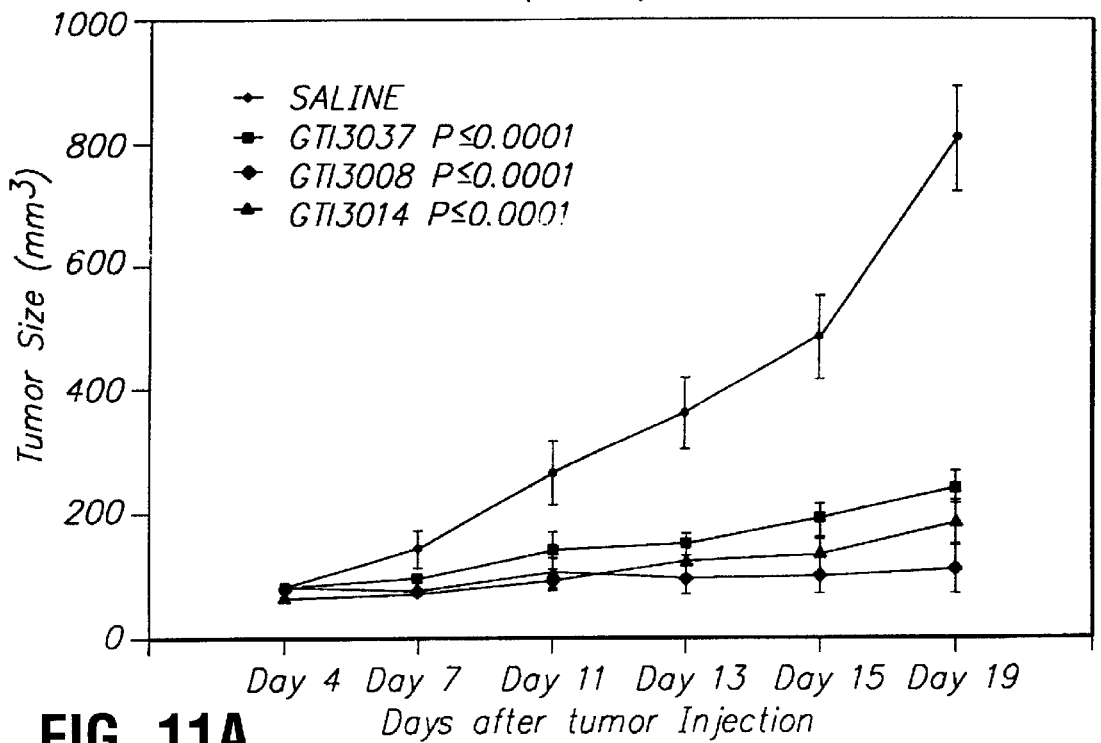
FIG. 11A is a chart showing the size of a human tumor in nude mice over time after intravenous treatment of the mice every second day with the indicated antisense oligonucleotides.
Figure 11B:
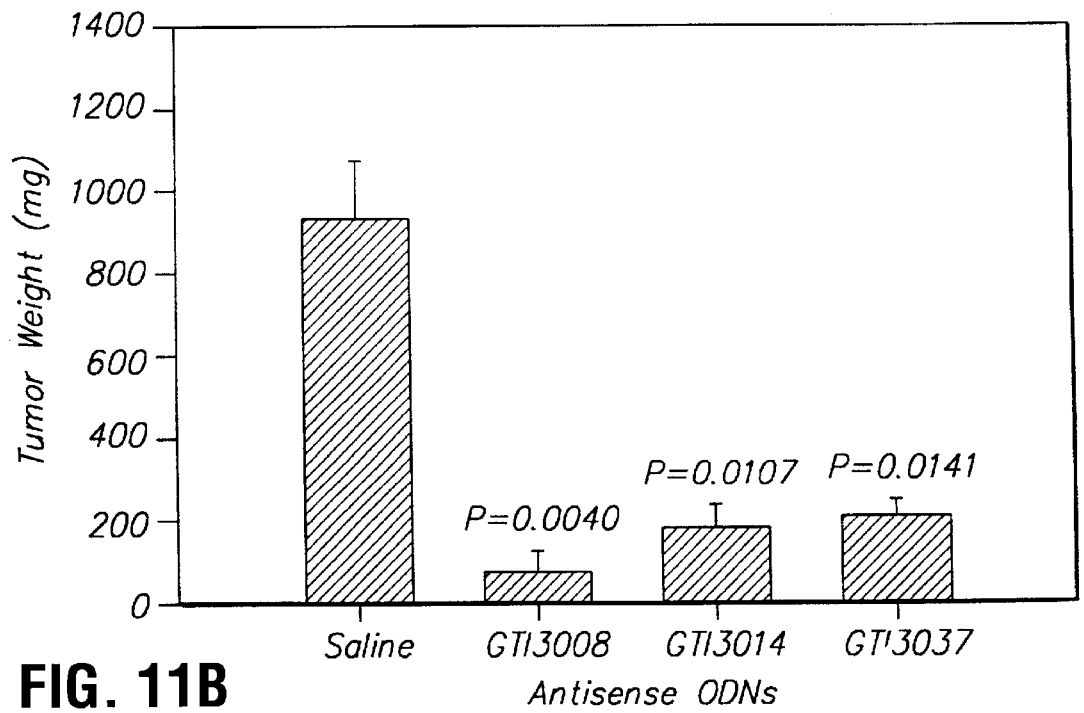
FIG. 11B is a graph of the weight of the human tumor removed from the mice approximately 10 days after intravenous treatment of the mice every second day with the indicated antisense oligonucleotides.

FIG. 11A shows the effects of the antisense oligonucleotides complementary to thioredoxin reductase on HT-29 tumor growth in CD-1 nude mice. Antitumor activities were estimated by the inhibition of tumor volume, which was measured with a caliper on average at two day intervals over the span of 9 days. Each point in the figure represents mean tumor volume calculated from 5 animals per experimental group. At the end of the treatment (usually 24 hours after the last treatment) the animals were sacrificed and tumor weights were measured. FIG. 11B shows the mean weight of the tumors. The antisense oligonucleotides showed significant inhibitory effects on tumor growth. When compared to the saline control each antisense oligonucleotide shown in FIG. 11A inhibited the growth of the tumor with a p value of ≦0.0001. When tumor weight was compared, each of the antisense oligonucleotides also showed statistically significant inhibition when compared to the saline control with p values of ≦0.0141. (FIG. 11B)

Example 11

Figure 12:
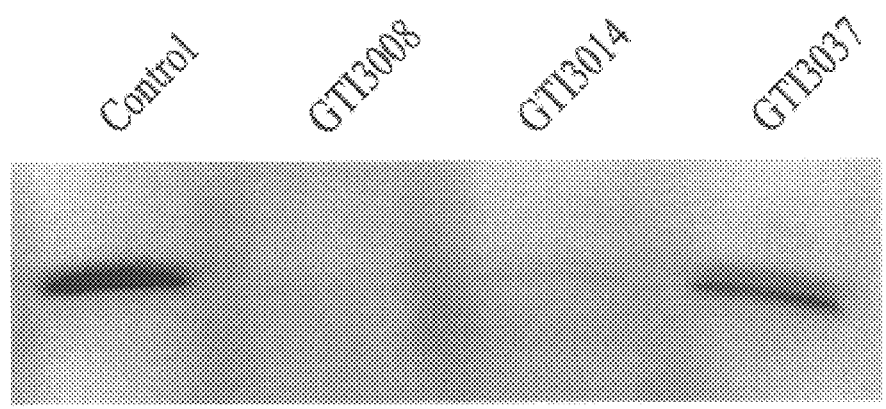
FIG. 12 is photograph of a Western blot showing the level of thioredoxin reductase protein expression in the human colon cancer HT-29 tumors excised from the nude mice approximately 10 days after intravenous treatment of the mice every second day with the indicated antisense oligonucleotides.

Reduction in Thioredoxin Reductase Protein Levels in Human Tumors in Mice by Intravenous Treatment with Antisense Oligonucleotides HT-29 human colon cancer cells (typically 3×10$^6$ cells in 100 µl of PBS) were subcutaneously injected into the right flank of 6–7 weeks old CD-1 athymic female nude mice. After the size of tumor reached an approximate volume of 100 mm$^3$, typically 5 days post tumor cell injection, different antisense oligonucleotides were administered by bolus infusion into the tail vein every other day at 10 mg/kg. Control animals received saline alone for the same period. Mice were sacrificed after 8 injections and excised tumor fragments of similar size were immediately collected into RIPA extraction buffer (50 mM Tris-HCl, pH 7.5, 150 mM NaCl, 1% NP-40, 0.5% sodium deoxycholate, 0.1% SDS, 0.02% NaN$_3$, 1 mM PMSF and 10 µM leupeptin) and rapidly homogenized for protein preparation. To measure th effects of antisense oligonuicleotides on thioredoxin reductase protein levels, Western blot analysis was performed as previously described (Choy et al.[29] and Fan et al.[30]) with some modifications. The protein extracts (10–20 µg) were fractionated on a 12% SDS-PAGE gel, transferred to nitrocellulose membranes and visualized by India ink staining. The expression of thioredoxin reductase was detected with anti-thioredoxin reductase antibody (0.2–1 µg/ml) (Research Genetics, Inc., Huntsville, Ala.) followed by horseradish peroxidase-conjugated antigoat IgG (Sigma, St. Louis, Mo.) at a dilution of 1:8,000. A protein of approximately 50 kDa was visualized by ECL (Amersham, Arlington Heights, Ill.). Protein loading in each lane was approximately the same. See FIG. 12.

---

What is claimed is:

1. An antisense oligonucleotide, or analogue thereof, comprising from about 17 to about 50 nucleotides that are complementary to a mRNA encoding a protein of a human thioredoxin system, wherein said oligonucleotide inhibits expression of said mRNA and wherein said protein is selected from the group consisting of thioredoxin and thioredoxin reductase, wherein the oligonucleotide, or analogue thereof, comprises a sequence as set forth in any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65 or 66, and wherein said analogue comprises at least one modified base selected from the group consisting of xanthine, hypoxanthine, 2-aminoadenine, 6-methyl adenine, 2-propyl adenine, 5-halo-uracil, 5-halo-cytosine, 6-aza uracil, 6-aza cytosine, 6-aza thymine, pseudo uracil, 4-thiouracil, 8-halo adenine, 8-aminoadenine, 8-thiol adenine, 8-hydroxyl adenine, 8-halo guanine, 8-amino guanine, 8-thiol guanine, 8-hydroxyl guanine, 5-trifluoromethyl uracil, and 5-trifluoro cytosine; at least one phosphorothioate, phosphotriester, methyl phosphonate, or phosphorodithioate internucleotide linkages; at least one short chain alkyl or cycloalkyl intersugar linkages; a morpholino backbone structure; or a peptide nucleic acid.

2. A vector comprising a nucleic acid encoding the antisense oligonucleotide according to claim 1.

3. A pharmaceutical composition comprising a pharmaceutically acceptable excipient and an effective amount of the antisense oligonucleotide, or analogue thereof, according to claim 1.

4. A method for inhibiting the growth of a human tumor comprising administering to a human suspected of having the tumor an effective amount of the is antisense oligonucleotide, or analog thereof, according to claim 1, under conditions such that the growth of the tumor is inhibited.

5. The method according to claim 4 further comprising the step of administering to the human a chemotherapeutic agent.

6. The method according to claim 4 wherein the oligonucleotide, or analog thereof, is nuclease resistant.

7. The antisense oligonucleotide according to claim 1, wherein the oligonucleotide, or analog thereof, is nuclease resistant.

8. The antisense oligonucleotide according to claim 1, wherein said analog comprises at least one phosphorothioate internucleotide linkage.

9. The antisense oligonucleotide according to claim 8, wherein the phosphorothioate internucleotide linkages link four, five or six 3'-terminus nucleotides of the analog.

10. The antisense oligonucleotide analog according to claim 8, wherein the phosphorothioate internucleotide linkages link all of the nucleotides of the analog.

11. The antisense oligonucleotide according to claim 1, wherein, in said analog, said alkyl intersugar linkage is selected from the group consisting of methyl, ethyl, n-propyl, iso-propyl, n-butyl, iso-butyl and n-hexyl.

12. The antisense oligonucleotide according to claim 1, wherein, in said analog, said cycloalkyl intersugar linkage is selected from the group consisting of cyclopropyl, cyclobutyl, cyclopentyl, cyclooctyl and adamantanyl.

13. The antisense oligonucleotide according to claim 1, wherein said analog is in a liposome.

* * * * *

SEQUENCE LISTING

```
<160> NUMBER OF SEQ ID NOS: 74

<210> SEQ ID NO 1
<211> LENGTH: 20
<212> TYPE: DNA
<213> ORGANISM: Human

<400> SEQUENCE: 1
tccaaagcac caaacagagc                                                    20

<210> SEQ ID NO 2
<211> LENGTH: 17
<212> TYPE: DNA
<213> ORGANISM: Human

<400> SEQUENCE: 2
gatggaaatg gatccaa                                                       17

<210> SEQ ID NO 3
<211> LENGTH: 20
<212> TYPE: DNA
<213> ORGANISM: Human
```

-continued

```
<400> SEQUENCE: 3
taaggaccga tggaaatgga                                                    20

<210> SEQ ID NO 4
<211> LENGTH: 20
<212> TYPE: DNA
<213> ORGANISM: Human

<400> SEQUENCE: 4
gacgagcggc tgtaaggacc                                                    20

<210> SEQ ID NO 5
<211> LENGTH: 20
<212> TYPE: DNA
<213> ORGANISM: Human

<400> SEQUENCE: 5
ttggctgctg gagtctgacg                                                    20

<210> SEQ ID NO 6
<211> LENGTH: 20
<212> TYPE: DNA
<213> ORGANISM: Human

<400> SEQUENCE: 6
gcttcaccat cttggctgct                                                    20

<210> SEQ ID NO 7
<211> LENGTH: 20
<212> TYPE: DNA
<213> ORGANISM: Human

<400> SEQUENCE: 7
gctctcgatc tgcttcacca                                                    20

<210> SEQ ID NO 8
<211> LENGTH: 20
<212> TYPE: DNA
<213> ORGANISM: Human

<400> SEQUENCE: 8
gcgtccaagg cttcctgaaa                                                    20

<210> SEQ ID NO 9
<211> LENGTH: 20
<212> TYPE: DNA
<213> ORGANISM: Human

<400> SEQUENCE: 9
gtttatcacc tgcagcgtcc                                                    20

<210> SEQ ID NO 10
<211> LENGTH: 20
<212> TYPE: DNA
<213> ORGANISM: Human

<400> SEQUENCE: 10
acgtggctga gaagtcaact                                                    20

<210> SEQ ID NO 11
<211> LENGTH: 20
<212> TYPE: DNA
<213> ORGANISM: Human
```

<400> SEQUENCE: 11
gatcattttg caaggcccac                                               20

<210> SEQ ID NO 12
<211> LENGTH: 20
<212> TYPE: DNA
<213> ORGANISM: Human

<400> SEQUENCE: 12
ggcttgatca ttttgcaagg                                               20

<210> SEQ ID NO 13
<211> LENGTH: 20
<212> TYPE: DNA
<213> ORGANISM: Human

<400> SEQUENCE: 13
agggaatgaa agaaaggctt                                               20

<210> SEQ ID NO 14
<211> LENGTH: 20
<212> TYPE: DNA
<213> ORGANISM: Human

<400> SEQUENCE: 14
tcacgttgga atacttttca                                               20

<210> SEQ ID NO 15
<211> LENGTH: 20
<212> TYPE: DNA
<213> ORGANISM: Human

<400> SEQUENCE: 15
catccacatc tacttcaagg                                               20

<210> SEQ ID NO 16
<211> LENGTH: 20
<212> TYPE: DNA
<213> ORGANISM: Human

<400> SEQUENCE: 16
tctgaagcaa catcctgaca                                               20

<210> SEQ ID NO 17
<211> LENGTH: 20
<212> TYPE: DNA
<213> ORGANISM: Human

<400> SEQUENCE: 17
ggcatgcatt tgacttcaca                                               20

<210> SEQ ID NO 18
<211> LENGTH: 20
<212> TYPE: DNA
<213> ORGANISM: Human

<400> SEQUENCE: 18
tcacccacct tttgtccctt                                               20

<210> SEQ ID NO 19
<211> LENGTH: 18
<212> TYPE: DNA

-continued

```
<213> ORGANISM: Human

<400> SEQUENCE: 19
ggcttcaagc ttttcctt                                              18

<210> SEQ ID NO 20
<211> LENGTH: 20
<212> TYPE: DNA
<213> ORGANISM: Human

<400> SEQUENCE: 20
atattttcag aaacatgatt                                            20

<210> SEQ ID NO 21
<211> LENGTH: 20
<212> TYPE: DNA
<213> ORGANISM: Human

<400> SEQUENCE: 21
caatggctgg ttatattttc                                            20

<210> SEQ ID NO 22
<211> LENGTH: 20
<212> TYPE: DNA
<213> ORGANISM: Human

<400> SEQUENCE: 22
gttttaaata gctcaatggc                                            20

<210> SEQ ID NO 23
<211> LENGTH: 20
<212> TYPE: DNA
<213> ORGANISM: Human

<400> SEQUENCE: 23
ttaaaaaaat tacaagtttt                                            20

<210> SEQ ID NO 24
<211> LENGTH: 20
<212> TYPE: DNA
<213> ORGANISM: Human

<400> SEQUENCE: 24
gcaactgggt ttatgtcttc                                            20

<210> SEQ ID NO 25
<211> LENGTH: 20
<212> TYPE: DNA
<213> ORGANISM: Human

<400> SEQUENCE: 25
tcacgcagat ggcaactggg                                            20

<210> SEQ ID NO 26
<211> LENGTH: 20
<212> TYPE: DNA
<213> ORGANISM: Human

<400> SEQUENCE: 26
gttttattgt cacgcagatg                                            20

<210> SEQ ID NO 27
<211> LENGTH: 20
```

```
<212> TYPE: DNA
<213> ORGANISM: Human

<400> SEQUENCE: 27
cccgacgcag agcttacaag                                               20

<210> SEQ ID NO 28
<211> LENGTH: 20
<212> TYPE: DNA
<213> ORGANISM: Human

<400> SEQUENCE: 28
gctcgcggct ttgtctggtt                                               20

<210> SEQ ID NO 29
<211> LENGTH: 20
<212> TYPE: DNA
<213> ORGANISM: Human

<400> SEQUENCE: 29
ccgtcccccg cgtgctccca                                               20

<210> SEQ ID NO 30
<211> LENGTH: 20
<212> TYPE: DNA
<213> ORGANISM: Human

<400> SEQUENCE: 30
gctgtcgtcc ccgccggcag                                               20

<210> SEQ ID NO 31
<211> LENGTH: 20
<212> TYPE: DNA
<213> ORGANISM: Human

<400> SEQUENCE: 31
ctgctgcacc caggcgcaat                                               20

<210> SEQ ID NO 32
<211> LENGTH: 20
<212> TYPE: DNA
<213> ORGANISM: Human

<400> SEQUENCE: 32
tcttcccttc cccgagacgc                                               20

<210> SEQ ID NO 33
<211> LENGTH: 20
<212> TYPE: DNA
<213> ORGANISM: Human

<400> SEQUENCE: 33
ccgtctgctc agacacgcct                                               20

<210> SEQ ID NO 34
<211> LENGTH: 20
<212> TYPE: DNA
<213> ORGANISM: Human

<400> SEQUENCE: 34
ccgcacacgc cacgaagctg                                               20

<210> SEQ ID NO 35
```

-continued

```
<211> LENGTH: 20
<212> TYPE: DNA
<213> ORGANISM: Human

<400> SEQUENCE: 35
gaagctttgt gtgaccgggt                                              20

<210> SEQ ID NO 36
<211> LENGTH: 20
<212> TYPE: DNA
<213> ORGANISM: Human

<400> SEQUENCE: 36
tcagggcccg accgtcctca                                              20

<210> SEQ ID NO 37
<211> LENGTH: 20
<212> TYPE: DNA
<213> ORGANISM: Human

<400> SEQUENCE: 37
gcagatcggt ttccgcggcc                                              20

<210> SEQ ID NO 38
<211> LENGTH: 20
<212> TYPE: DNA
<213> ORGANISM: Human

<400> SEQUENCE: 38
ggttggacca tggccgccta                                              20

<210> SEQ ID NO 39
<211> LENGTH: 20
<212> TYPE: DNA
<213> ORGANISM: Human

<400> SEQUENCE: 39
agggccgttc atttttagta                                              20

<210> SEQ ID NO 40
<211> LENGTH: 20
<212> TYPE: DNA
<213> ORGANISM: Human

<400> SEQUENCE: 40
agatcttcag ggccgttcat                                              20

<210> SEQ ID NO 41
<211> LENGTH: 20
<212> TYPE: DNA
<213> ORGANISM: Human

<400> SEQUENCE: 41
agcagctgcc agacctcctg                                              20

<210> SEQ ID NO 42
<211> LENGTH: 20
<212> TYPE: DNA
<213> ORGANISM: Human

<400> SEQUENCE: 42
caagaggggt gggagtgaca                                              20
```

```
<210> SEQ ID NO 43
<211> LENGTH: 20
<212> TYPE: DNA
<213> ORGANISM: Human

<400> SEQUENCE: 43
tttcgagagt cttgcagggc                                               20

<210> SEQ ID NO 44
<211> LENGTH: 20
<212> TYPE: DNA
<213> ORGANISM: Human

<400> SEQUENCE: 44
ctcggtagcc ccaattcaaa                                               20

<210> SEQ ID NO 45
<211> LENGTH: 20
<212> TYPE: DNA
<213> ORGANISM: Human

<400> SEQUENCE: 45
ttgtcaccag ggatgcccaa                                               20

<210> SEQ ID NO 46
<211> LENGTH: 20
<212> TYPE: DNA
<213> ORGANISM: Human

<400> SEQUENCE: 46
tccaaagcga cataggatgc                                               20

<210> SEQ ID NO 47
<211> LENGTH: 20
<212> TYPE: DNA
<213> ORGANISM: Human

<400> SEQUENCE: 47
cctattgcca gcatcaccgt                                               20

<210> SEQ ID NO 48
<211> LENGTH: 20
<212> TYPE: DNA
<213> ORGANISM: Human

<400> SEQUENCE: 48
ctggattgca actggggtga                                               20

<210> SEQ ID NO 49
<211> LENGTH: 20
<212> TYPE: DNA
<213> ORGANISM: Human

<400> SEQUENCE: 49
cctcagaaag gccacaagca                                               20

<210> SEQ ID NO 50
<211> LENGTH: 20
<212> TYPE: DNA
<213> ORGANISM: Human

<400> SEQUENCE: 50
ttgagcgcag ctgcaaagcc                                               20
```

<210> SEQ ID NO 51
<211> LENGTH: 20
<212> TYPE: DNA
<213> ORGANISM: Human

<400> SEQUENCE: 51
gagcgcttgg tcacagacaa                                               20

<210> SEQ ID NO 52
<211> LENGTH: 20
<212> TYPE: DNA
<213> ORGANISM: Human

<400> SEQUENCE: 52
aacagcatcc acactggggc                                               20

<210> SEQ ID NO 53
<211> LENGTH: 20
<212> TYPE: DNA
<213> ORGANISM: Human

<400> SEQUENCE: 53
gcacggaaac gagccagtgg                                               20

<210> SEQ ID NO 54
<211> LENGTH: 20
<212> TYPE: DNA
<213> ORGANISM: Human

<400> SEQUENCE: 54
acgcaggtgc caagagccca                                               20

<210> SEQ ID NO 55
<211> LENGTH: 20
<212> TYPE: DNA
<213> ORGANISM: Human

<400> SEQUENCE: 55 gtgacccccag tgtgatgctg                                              20

<210> SEQ ID NO 56
<211> LENGTH: 20
<212> TYPE: DNA
<213> ORGANISM: Human

<400> SEQUENCE: 56
tcgatgccct gccaaatgtc                                               20

<210> SEQ ID NO 57
<211> LENGTH: 20
<212> TYPE: DNA
<213> ORGANISM: Human

<400> SEQUENCE: 57
acagttgttc catcaccgcc                                               20

<210> SEQ ID NO 58
<211> LENGTH: 20
<212> TYPE: DNA
<213> ORGANISM: Human

<400> SEQUENCE: 58
tcccttccat gcaacaagac                                               20

<210> SEQ ID NO 59
<211> LENGTH: 20
<212> TYPE: DNA
<213> ORGANISM: Human

<400> SEQUENCE: 59
tttcccggga caagcctaca                                               20

<210> SEQ ID NO 60
<211> LENGTH: 20
<212> TYPE: DNA
<213> ORGANISM: Human

<400> SEQUENCE: 60
gcacacaggg gcaaatttgg                                               20

<210> SEQ ID NO 61
<211> LENGTH: 20
<212> TYPE: DNA
<213> ORGANISM: Human

<400> SEQUENCE: 61
ctaccaaatg ccaggcaatg                                               20

<210> SEQ ID NO 62
<211> LENGTH: 20
<212> TYPE: DNA
<213> ORGANISM: Human

<400> SEQUENCE: 62
tgtttctccc ccatttctgg                                               20

<210> SEQ ID NO 63
<211> LENGTH: 20
<212> TYPE: DNA
<213> ORGANISM: Human

<400> SEQUENCE: 63
gttccctgag gtggcccaga                                               20

<210> SEQ ID NO 64
<211> LENGTH: 20
<212> TYPE: DNA
<213> ORGANISM: Human

<400> SEQUENCE: 64
acggtcaggg gctctgctgc                                               20

<210> SEQ ID NO 65
<211> LENGTH: 20
<212> TYPE: DNA
<213> ORGANISM: Human

<400> SEQUENCE: 65
atgaggacgt gaggcagagc                                               20

<210> SEQ ID NO 66
<211> LENGTH: 20
<212> TYPE: DNA
<213> ORGANISM: Human

<400> SEQUENCE: 66

-continued

```
tggtcaactg cctcaattgc                                                   20

<210> SEQ ID NO 67
<211> LENGTH: 581
<212> TYPE: DNA
<213> ORGANISM: Human
<220> FEATURE:
<221> NAME/KEY: CDS
<222> LOCATION: (79)..(396)

<400> SEQUENCE: 67
agtcttgaag ctctgtttgg tgctttggat ccatttccat cggtccttac agccgctcgt        60
cagactccag cagccaag atg gtg aag cag atc gag agc aag act gct ttt        111
                    Met Val Lys Gln Ile Glu Ser Lys Thr Ala Phe
                     1               5                  10 cag gaa gcc ttg gac gct gca ggt gat aaa ctt gta gta gtt gac ttc        159
Gln Glu Ala Leu Asp Ala Ala Gly Asp Lys Leu Val Val Val Asp Phe
             15                  20                  25 tca gcc acg tgg tgt ggg cct tgc aaa atg atc aag cct ttc ttt cat        207
Ser Ala Thr Trp Cys Gly Pro Cys Lys Met Ile Lys Pro Phe Phe His
         30                  35                  40 tcc ctc tct gaa aag tat tcc aac gtg ata ttc ctt gaa gta gat gtg        255
Ser Leu Ser Glu Lys Tyr Ser Asn Val Ile Phe Leu Glu Val Asp Val
     45                  50                  55 gat gac tgt cag gat gtt gct tca gag tgt gaa gtc aaa tgc atg cca        303
Asp Asp Cys Gln Asp Val Ala Ser Glu Cys Glu Val Lys Cys Met Pro
 60                  65                  70                  75 aca ttc cag ttt ttt aag aag gga caa aag gtg ggt gaa ttt tct gga        351
Thr Phe Gln Phe Phe Lys Lys Gly Gln Lys Val Gly Glu Phe Ser Gly
                 80                  85                  90 gcc aat aag gaa aag ctt gaa gcc acc att aat gaa tta gtc taa            396
Ala Asn Lys Glu Lys Leu Glu Ala Thr Ile Asn Glu Leu Val
             95                 100                 105 tcatgtttct gaaatataa ccagccattg agctatttaa aacttgtaat ttttttaatt       456
tacaaaaata taaatatga agacataaac ccagttgcca tctgcgtgac aataaaacat        516
taatgctaac acttttaaa accgtctcat gtctgaatag ctttcaaaat aaatgtgaaa       576
tggtc                                                                 581

<210> SEQ ID NO 68
<211> LENGTH: 105
<212> TYPE: PRT
<213> ORGANISM: Human

<400> SEQUENCE: 68

Met Val Lys Gln Ile Glu Ser Lys Thr Ala Phe Gln Glu Ala Leu Asp
 1               5                  10                  15

Ala Ala Gly Asp Lys Leu Val Val Val Asp Phe Ser Ala Thr Trp Cys
             20                  25                  30

Gly Pro Cys Lys Met Ile Lys Pro Phe Phe His Ser Leu Ser Glu Lys
         35                  40                  45

Tyr Ser Asn Val Ile Phe Leu Glu Val Asp Val Asp Asp Cys Gln Asp
     50                  55                  60

Val Ala Ser Glu Cys Glu Val Lys Cys Met Pro Thr Phe Gln Phe Phe
 65                  70                  75                  80

Lys Lys Gly Gln Lys Val Gly Glu Phe Ser Gly Ala Asn Lys Glu Lys
                 85                  90                  95

Leu Glu Ala Thr Ile Asn Glu Leu Val
            100                 105
```

```
<210> SEQ ID NO 69
<211> LENGTH: 19
<212> TYPE: DNA
<213> ORGANISM: Human

<400> SEQUENCE: 69
cagatcgaga gcaagactg                                             19

<210> SEQ ID NO 70
<211> LENGTH: 20
<212> TYPE: DNA
<213> ORGANISM: Human

<400> SEQUENCE: 70
ttcattaatg gtggcttcaa                                            20

<210> SEQ ID NO 71
<211> LENGTH: 20
<212> TYPE: DNA
<213> ORGANISM: Human

<400> SEQUENCE: 71
cgcggggctc tccagaacat                                            20

<210> SEQ ID NO 72
<211> LENGTH: 20
<212> TYPE: DNA
<213> ORGANISM: Human

<400> SEQUENCE: 72
gcaatgccag ccccagcgtc                                            20

<210> SEQ ID NO 73
<211> LENGTH: 20
<212> TYPE: DNA
<213> ORGANISM: Human

<400> SEQUENCE: 73
ttggcttaga aaccgtaggg                                            20

<210> SEQ ID NO 74
<211> LENGTH: 20
<212> TYPE: DNA
<213> ORGANISM: Human

<400> SEQUENCE: 74
ccaatggcca aaagtaacta                                            20
```